United States Patent [19]
Eisen et al.

[11] Patent Number: 5,939,724
[45] Date of Patent: *Aug. 17, 1999

[54] LIGHT WEIGHT-CAMERA HEAD AND-CAMERA ASSEMBLIES CONTAINING IT

[75] Inventors: Yosef Eisen, Nes Ziona; Chaim Gilat, Rehovot; Giora Keinan, Rishon-LeZion, all of Israel

[73] Assignee: State of Israel, The, Atomic Energy Commission, Soreo Nuclear Research Center, Yavne, Israel

[*] Notice: This patent is subject to a terminal disclaimer.

[21] Appl. No.: 08/768,840

[22] Filed: Dec. 18, 1996

Related U.S. Application Data

[63] Continuation-in-part of application No. 08/257,876, Jun. 10, 1994, Pat. No. 5,587,585, which is a continuation-in-part of application No. 08/157,713, Nov. 24, 1993, Pat. No. 5,365,069.

[30] Foreign Application Priority Data

Jun. 2, 1993 [IL] Israel ..................................... 105881

[51] Int. Cl.$^6$ ....................................................... G01T 1/24
[52] U.S. Cl. .................................. 250/370.09; 250/363.1
[58] Field of Search ............................ 250/370.09, 363.1

[56] References Cited

U.S. PATENT DOCUMENTS

| | | | |
|---|---|---|---|
| 4,047,037 | 9/1977 | Schlosser et al. | 250/370.09 |
| 4,055,765 | 10/1977 | Gerber et al. | 250/370.09 |
| 4,061,919 | 12/1977 | Miller et al. | 250/370.09 |
| 4,529,882 | 7/1985 | Lee | 250/370.09 |
| 4,672,207 | 6/1987 | Derenzo | 250/363.02 |
| 5,206,512 | 4/1993 | Iwao | 250/363.04 |
| 5,210,421 | 5/1993 | Gullberg et al. | 250/363.04 |
| 5,252,830 | 10/1993 | Weinberg | 250/363.02 |
| 5,278,416 | 1/1994 | Pierfitte | 250/363.08 |
| 5,365,069 | 11/1994 | Eisen et al. | 250/370.09 |
| 5,587,585 | 12/1996 | Eisen et al. | 250/370.09 |

OTHER PUBLICATIONS

Schlosser et al., "A Practical Gamma–Ray Camera System Using High Purity Germanium," IEEE Tans Nuc. Sci. vol Ns 21 No. #1 1974 pp. 658–664.

Lim et al., "Triangular Spect System For 3–D Total Origin Volume Imaging: Design Concept and Preliminary Results" IEEE Trans Nuc Sci. vol. NS.32 No.1 Feb. 1985 pp. 741–747.

Physics in Nuclear Medicine (Second Edition), J.A. Sorenson and M.E. Phelps, W.B Saunders Company, Philadelphia, U.S. (1987),pp. 298–300, 317.

"A Third Generation Digital Gamma Camera", D.W. Heyda, F.R. Croteau, T.A, Govaert, SPIE, vol. 454 Application of Optical Instrumentation in Medicine (1984),pp. 478–484.

"The Use of Multiwire Proportional Counters to Select and Localize Charged Particles", G. Charpak, R. Bouclier, T. Bressani, J. Favier, C. Zupanic, Nuclear Instruments and Methods, vol. 62 (1968) pp.262–268.

Practical Nuclear Medicine, E.L. Palmer, J.A. Scott, H.W. Strauss, W.B. Saunders Company, U.S. (1992), pp. 27–69.

"A Gamma Camera for Medical Applications, using a Multiwire Proportional Counter", J.L. Lacy, A.D. Le Blanc, J.W. Babich, M.W. Bungo, L.A. Latson, R.M. Lewis, Journal of Nuclear Medicine, vol. 25, No. 9. Sep. 1984, pp. 1003–1012.

"Slot–beam Digital Mammography Using a Time Delay Integration (TDI) CCD", D.W. Holdsworth et al., SPIE, vol. 1090 Medical Imaging III: Image Formation(1989), pp. 306–313).

*Primary Examiner*—Constantine Hannaher
*Attorney, Agent, or Firm*—Steinberg & Raskin, P.C.

[57] ABSTRACT

A light weight gamma-camera head and assemblies and kits which embody it. The gamma-camera head has a detector assembly which includes an array of room temperature, solid state spectroscopy grade detectors each associated with a collimator and preamplifier, which detectors and associated collimators and preamplifiers are arranged in parallel rows extending in a first direction and suitably spaced from each other in a second direction normal to the first direction, each of the parallel detector rows holding a plurality of detectors. The head may optionally have an electric motor for moving the detector in the second direction and optionally also in the first direction, either stepwise or continuously.

33 Claims, 21 Drawing Sheets

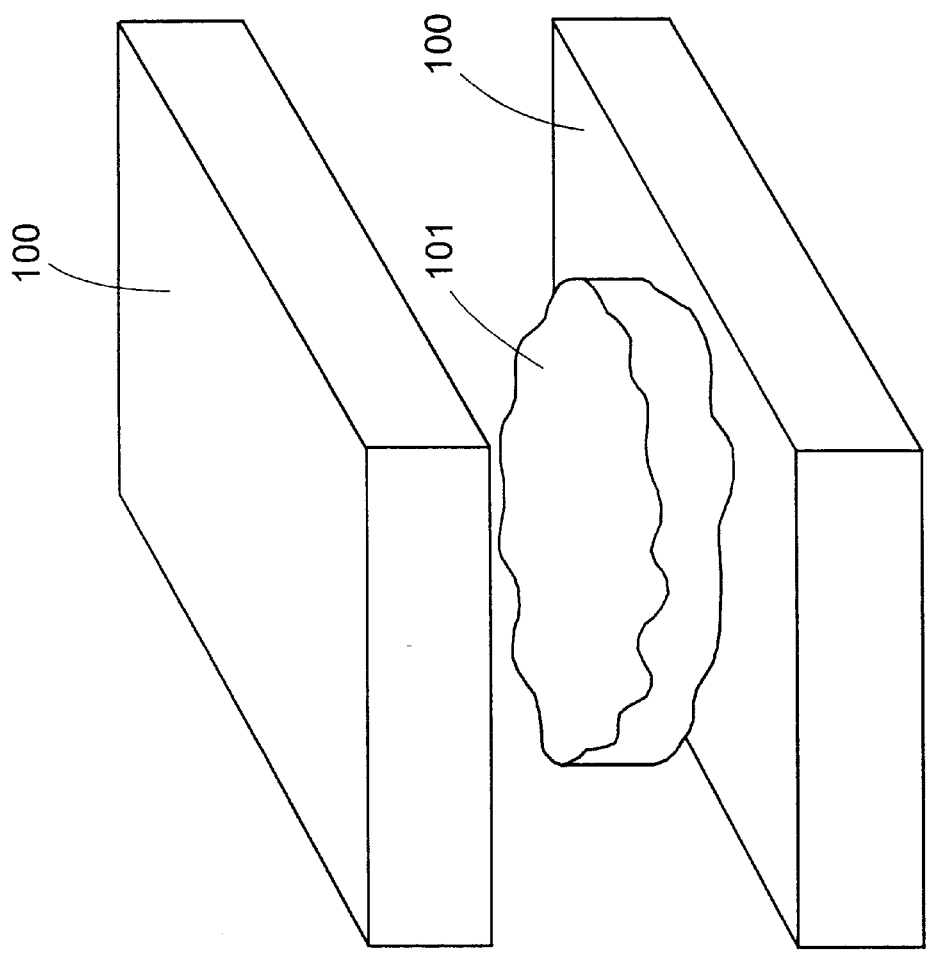

LIGHT WEIGHT-CAMERA HEAD AND-CAMERA ASSEMBLIES CONTAINING IT

This application is a continuation-in-part of U.S. patent application Ser. No. 08/257,876 filed Jun. 10, 1994, now U.S. Pat. No. 5,587,585, which in turn is a continuation-in-part of U.S. patent application Ser. No. 08/157,713 filed Nov. 24, 1993, now U.S. Pat. No. 5,365,069.

FIELD OF THE INVENTION

The present invention is in the field of radionuclide imaging. Radionuclide imaging is one of the most important applications of radioactivity in medicine and it aims to obtain a map of the distribution of radioactivity within an organ of a patient upon injection of a substance that bears a so-called radionuclide, i.e. a radioactive marker. Imaging is obtained with the aid of instruments, referred to in the art as gamma-cameras, which bear detectors for x-rays and gamma-radiation originating from the radioactive marker substance.

BACKGROUND OF THE INVENTION AND PRIOR ART

Prior art reviews are to be found in the text book "Physics in Nuclear Medicine" (1987) by J. A. Sorenson and M. E. Phelps, W. B. Saunders Company, Philadelphia, U.S.A. (second edition).

The very first imaging system was based on a scintillation crystal coupled to a photomultiplier tube with a proper collimator in front of the scintillator. The image was obtained by a raster movement, i.e. a rectilinear scanning back and forth over the area of interest on the patient, incrementing a short distance between scan passes. This system is inefficient and time consuming.

By way of improvement of the above scanner-type imaging system a multicrystal scanner was developed, which in one configuration contains an array of scintillators each coupled to a photomultiplier. In another configuration of such a γ-camera, instead of individual photomultiplier tubes for each crystal there is provided one photomultiplier for each row and one for each column. Location of each scintillation is determined from the location of the row and column intersection.

By yet another configuration described by B. W. Heyda, F. R. Croteau, T. A. Govaert, SPIE, vol. 454 (1984) p. 478, a single crystal is slotted to create the equivalent of an array of 20×20 individual detector elements. Each element is surrounded by reflective material and is associated with a small number of photomultiplier tubes.

The most commonly used scintillation detector γ-camera is an instrument originally developed by Anger. An image of an organ in the body is formed on a large scintillation crystal by means of a collimator. Various types of collimators may be used, such as for instance parallel, converging or diverging, in order to identify the location from which the γ-ray is emitted. The scintillation, which occurs when the γ-rays interact with the scintillator material, are viewed by a matrix of photomultiplier tubes. The computing circuit determines the location of scintillating the crystal. The coordinates of each scintillation are recorded and scintillations are accumulated and are displayed in real time on a video screen. Dynamic studies of an organ can be performed by generating a series of time-sequenced images.

Scintillation-type γ-cameras have some inherent shortcomings. Thus, as for any scintillation device, the energy of the incident photon absorbed in the scintillator is transformed to light with relatively low efficiency. Thereafter, the energy resolution of the scintillator such as a NaI(Tl) scintillator, which reflects the fluctuations in the emitted light quanta, is of the order of 16% Full Width Half Maximum (FWHM) for 60 keV, and about 12% for 140.5 keV photons. Such relatively poor energy resolution affects both the intrinsic spatial resolution and the intrinsic efficiency. If scattered light were to be rejected in order to improve spatial resolution, a narrow energy window must be selected whereby the intrinsic efficiency is reduced.

Furthermore, there is an image non-linearity in both the X and Y directions manifested as the so-called pincushion and barrel distortions. These distortions are primarily due to the finite size of the photomultiplier tube, which causes different light collection efficiencies for events which occur near the edge and near the center of the photomultiplier tube.

Still further, the intrinsic spatial resolution is limited, mainly by the following four factors:

(i) Compton scattering inside the detector sometimes results in an absorbed scattered photon to be detected at a far distance from the point of interaction. Therefore the scattered photon and the Compton electron are recorded as a single event at a location between the original point of interaction in the crystal and the point of interaction of the Compton photon.

(ii) Statistical fluctuations in the distribution of light photons between photomultiplier tubes from one scintillation event to the next one, cause deterioration of the spatial resolution. This effect increases with a decrease in photon energy. For instance, intrinsic spatial resolution using $^{99m}$Tc (140.5 keV) is better than with $^{201}$Tl (69–80.3 keV).

(iii) Intrinsic spatial resolution deteriorates with the increase of the crystal thickness.

(iv) The intrinsic spatial resolution also depends on the size and on the packing ratio of the photomultiplier tubes.

Yet another shortcoming of the scintillation type γ-camera is that at high count rates above 100 k counts/sec/area of detector, images are distorted due to pile up. Attempts have been made to introduce pile-up corrections, but this leads either to reduction in statistics or to reduction in the amount of integrated charge, thus decreasing the energy resolution and also causing degradation in the intrinsic spatial resolution.

Finally, because of the need for shielding both the scintillators and individual photomultiplier tubes which, due to the relatively large volume of the latter, requires a considerable amount of shielding material, the total weight of the camera head is high and may reach 80 kg. Such a high weight imposes several operational restrictions, makes mobile scintillation γ-cameras cumbersome and heavy and makes it impossible to provide portable scintillation type γ-cameras.

There are also known γ-cameras which instead of scintillation detectors, have detectors based on gas filled multi-wire proportional chambers (MWPC) and such detectors are described, for example, by G. Charpak et al., Nuclear Instr. and Meth. 62 (1968) 262, and by J. L. Lacy, et al, J. of Nuc. Medicine 25 (1984) 1004. In the classical MWPC structure, electrons released by ionization in the gas are multiplied in the high field region created around the wires inside the chamber. In order to obtain reasonable efficiency, the detection region is filled with high atomic number gas e.g. xenon, and pressurized to about 5 atmospheres. The drifting ionization is collected at the anode.

Various methods can be used in the MWPC type γ-cameras to obtain localization over extended surface area, the most common one being based on signals arriving via an external delay line. Lacy et al measured the spatial resolution by detecting the signal induced in the two cathode grids which are orthogonally oriented to each other. The four time delays obtained from the delay lines are digitized by high speed counters which are gated by the anode signal and gated off by the delay line outputs.

γ-cameras with MWPC type detectors also have some drawbacks. Thus, the intrinsic efficiency of MWPC depends on the atomic number of the gas and on its density inside the chamber. Xenon, which is the noble gas usually used, has an atomic number greater than that of NaI(Tl), the scintillator usually used in an Anger scintillation type camera. However, in order to achieve high quantum efficiencies, high pressures of the order of 25 atmospheres would be required but such high pressures are dangerous. Therefore, for practical reasons the gas pressure inside the chambers of a MWPC type γ-camera does, as a rule, not exceed 5 atmospheres and as a result the intrinsic efficiency at 140.5 keV is only about 10%.

Moreover, hermetically sealed MWPC's often show deterioration in time due to gas contamination, mainly of water and oxygen molecules resulting from outgassing of detector materials. This contamination dramatically affects the charge collection efficiency.

Yet another problem inherent in γ-cameras with MWPC type detectors is lack of satisfactory energy resolution. The energy resolution depends on the number of electron-ion pairs created in the gas per energy deposited in the interaction. The energy necessary to create an electron-ion pair in the gas is of the order of 30 eV. This relatively high energy causes the energy resolution to be comparable to or worse than that of a NaI(Tl) scintillator.

Still another problem is related to the escape of Kα photons of about 29 keV from the point of interaction, often out of the detector. Accordingly, the probability to obtain in one peak the full energy deposited in the gas is quite small. For short distances of anode-to-cathode wire spacings the escape peak always dominates the spectrum. If the escape peak is recorded instead of the full energy peak, it may overlap the scattered photons which have lower energies than the incident energy.

Finally, also in γ-cameras with MWPC type detectors the camera head is quite heavy and does not lend itself for making the camera portable.

Patients with a need for radionuclide imaging are very often not in a position to be transported from their place of hospitalization to a γ-camera laboratory and accordingly, there has for a long time been felt a need to provide a small light weight mobile or portable, yet reliable γ-camera. So far this need was not met with the so-called mobile cameras and it is thus an object of the present invention to provide a light weight γ-camera head suitable for use in light weight mobile γ-camera.

It is a further object of the present invention to provide a portable camera head which together with the associated electronics and, if desired, a foldable stand such as a foldable and telescopic tripod, can be packed in hand carried bag or suitcase.

It is yet another object of the invention to provide a portable γ-camera head that can be attached to the body of a diagnosed subject.

Still further the invention provides a light weight γ-camera head for use in a stationary planar γ-camera.

Yet another object of the invention is to provide a light weight head for a Single Photon Emission Computed Tomography (SPECT) system.

To realize these and other objects, the present invention aims at providing a γ-camera in which the γ-radiation impinging on the detector produces directly electric signals with no intermediary conversion into a light scintillation, thereby increasing both the energy and spatial resolutions and enhancing the contrast.

These and other objects of the present invention will become apparent from the following description.

SUMMARY OF THE INVENTION

In accordance with the present invention it has been found that when x-rays and γ-radiation originating from the decay of a radionuclide impinge on room temperature spectroscopy grade solid state detectors, the resulting signals can be processed directly into an image without need for any intermediary light signal production.

It has further been found in accordance with the invention that use of room temperature, spectroscopy grade solid state detectors in the construction of a γ-camera head leads, among others to the following advantages.

(a) the energy resolution is significantly improved which provides for improved scatter removal and sensitivity;

(b) the intrinsic spatial resolution becomes independent of the energy of the incident radiation;

(c) there is no need for a position encoding system;

(d) a high count rate is attainable; and (e) thermal stabilization is quick.

Based on these findings, the invention provides a γ-camera head having a detector assembly for the detection of x-rays and γ-radiation, characterized by said detector assembly comprising an array of room temperature, solid state spectroscopy grade detectors each associated with collimator and charge sensitive preamplification means being a member selected from the group of preamplifiers, hybrid preamplifier/amplifier devices and Application Specific Integrated Circuits (ASIC) which detectors and preamplification means are arranged in parallel rows extending in a first direction and suitably spaced from each other in a second direction normal to said first direction, or in parallel detector assemblies each including at least two juxtaposed and mutually staggered detector rows, each of said parallel rows or assemblies holding a plurality of said room temperature spectroscopy grade solid state detectors;

If desired the γ-camera head according to the invention may comprise electric motor means for moving said detector assembly in said second direction in a controlled fashion.

In one form of a γ-camera head according to the invention, said collimator means are of the pinhole type. By one embodiment of this form, one single collimator which covers the entire field of view is associated with all detectors of the array. Alternatively, there may be provided several pinhole collimators aligned in at least one row extending in said first direction.

In another form, the γ-camera head comprises one single converging collimator which covers the entire field of view. Alternatively, a separate converging collimator may be provided for each row of detectors.

In yet another form, the γ-camera head according to the invention comprises one single diverging collimator covering the entire field of view. Alternatively, a separate diverging collimator may be provided for each row of detectors.

In cases of converging or diverging collimators, convergence or divergence, as the case may be, may be in said first and/or second direction.

In still another form, a γ-camera head according to the invention has a single parallel hole collimator that covers the entire field of view. Alternatively, a separate parallel hole collimator may be provided for each row of detectors.

The detectors and associated collimators and preamplifiers in a γ-camera head according to the invention are arranged in assemblies each comprising at least two juxtaposed and staggered detector rows and a plurality of such assemblies are arranged in parallel rows extending in a first direction and suitably spaced from each other in a second direction normal to said first direction.

In the embodiment of the invention which comprises electric motor means for moving said detector assembly in said second direction in a controlled fashion, the detector assembly may be moved either stepwise or continuously.

When the detector array is moved stepwise it alternates between rest and shifting periods, each rest period being sufficiently long, say 30 seconds, for acquiring the necessary image data, and the sum total of the data acquired during the shifting from the first to the last rest period render a continuous image. It was found in accordance with the invention that the non-continuous mode of data acquisition notwithstanding, the resulting efficiency and intrinsic spatial resolution are similar as in existing scintillation γ-cameras, using all purpose collimators.

When the detector assembly moves continuously data sampling is performed during predetermined time intervals.

The room temperature solid state spectroscopy grade detectors used in accordance with the invention are typically in the form of square platelets made for instance of CdTe, $CdZnTe$, $PbI_2$ or $HgI_2$.

In a γ-camera according to the invention the x-rays or γ-radiation may impinge on the detectors in parallel or perpendicular to the electric field direction.

The detector assembly in the camera head may cover in a single step a large portion of the useful field of view. This can be achieved by using monolithic arrays of detectors, e.g. in form of units containing each two adjacent rows of monolithic detector arrays each including a plurality of pad detector elements, which units form between them a two-dimensional detector array covering the complete field of view of the camera head; dense packing of the analog amplifier; and multiplexing logic electronics produced with technological means common in the art. The admissible density of analog amplifiers and logic electronics may depend on the desired counting rate and readout configuration. In case of a two-dimensional array of detectors covering the entire field of view, the said electric motor means may not be required.

For the sake of clarity it is noted that the term "array" is used herein in two different senses: for one, it is used as the conventional attribute of a monolithic detector having a plurality of pad detector elements and which are referred to in the art as "monolithic detector arrays"; and in addition the term is used to describe the arrangement of a plurality of monolithic detector array units in said detector assembly.

When scanning the area with detectors organized in groups of rows adjacent to each other, the Time Delay Integration technique, as employed already in digital mammography can be used. (See for example Holdsworth, D. W., Nishikawa, R. M., Mawdsley, G. E., Yaffe, M. J., Feuster, A., Slot beam digital mammography using a time-delay integration (TDI) CCD. Proc. SPIE, 1989; 1090, pp. 306–313). This technique is based on integrating the information for a given pixel, from the information acquired by the detectors of the different rows as they pass in front of that pixel. The Time Delay Integration technique is implemented in software and results in an improved signal to noise in the image.

Depending on requirements, the collimator means may be designed for parallel, converging or diverging propagation of the x-rays and γ-radiation and if desired a pinhole collimator may be used.

If desired, the γ-camera head according to the invention may also comprise electric motor means for moving said detector assembly in said first direction in a controlled fashion, either stepwise or continuously.

All the above features lead to a light-weight γ-camera.

The invention further provides a γ-camera assembly comprising a γ-camera head of the kind specified and at least one work station with a hardware/software combination comprising a man machine interface (MMI) module, a data acquisition module, an image construction module and an image processing and display module.

If desired, the camera head and work station may be remote from and linked to each other by any suitable communication links such as local area network (LAN), a telephone line and the like, via a remote station interface module.

A camera head according to the invention is comparatively light weight, e.g. weighing about 3 kg as compared to prior art γ-camera heads which may be as heavy as 80 kg. The low weight of the camera head results from having to shield only the small spectroscopy grade solid state detectors and not scintillators and large size photomultipliers. This reduced shielding requirement does not impair the sensitivity and efficiency of the camera and it is possible in accordance with the invention to achieve with a few rows of detectors and associated collimators sensitivity and efficiency for the complete field of view that are similar to those of existing γ-cameras.

In accordance with one embodiment of the invention, the camera head is mounted on the end of a foldable arm attached to a work station component, e.g. a trolley, and having a plurality of joints by which the head can be adjusted to the patient's body in any desired fashion. Alternatively, the camera head may be designed for attachment to the patient's body either alone or, if desired, together with a data acquisition module.

The γ-camera according to the invention has a good intrinsic spatial resolution, can function at count rates of even above $10^6$/sec in the area of detection and can be used for ECG gated or ungated radionuclide mapping measurements in an organ. The energy resolution of the spectroscopy grade solid state detectors used in the γ-camera according to the invention is much superior to that of scintillators and multiwire proportional chambers (MWPC) used in the prior art. For instance, the energy resolution at full width half maximum (FWHM) is 5% and 8% for 140.5 keV and 60 keV, respectively. Such superior energy resolution enables more efficient rejection of scattered γ-rays.

The γ-camera according to the invention is capable of monitoring radionuclides emitting γ-rays in the energy range of 20–180 keV and is thus suitable for use in conjunction with common radionuclides such as $^{201}$Tl (69–80.3 keV) and $^{99m}$Tc (140.5 keV).

The spatial resolution of a γ-camera according to the invention depends only on the size of the solid state detectors and the associated collimator and, as distinct from an Anger camera, does not depend on the energy of the incident γ-radiation. The intrinsic efficiency of each detector is high and amounts to 100% for 69–80.3 keV and up to 80% for 140.5 keV.

The electronics of the work station of a γ-camera according to the invention is also lightweight and occupies only a small volume. Accordingly it is possible in accordance with the invention to pack the camera head and the associated electronics and computer into hand-carried bags whereby the entire camera assembly is portable.

In a γ-camera according to the invention the position of an intersecting x-ray or γ-ray is determined by a single room temperature spectroscopy grade solid state detector and there is no need for a complicated position encoding system.

The light weight head according to the invention can also be mounted on stationary γ-cameras and can be adapted for use in a SPECT measurement, using a simple gantry or positioning the camera head in front of a diagnosed subject sitting on a rotating chair.

BRIEF DESCRIPTION OF THE DRAWINGS

For better understanding some embodiments of the invention will hereinafter be described, by way of example only, with reference to the annexed drawings in which:

FIG. 23 is a schematic illustration of a PET measurement configuration with two γ-camera heads according to the invention placed on opposite sides of an inspected organ.

DETAILED DESCRIPTION OF SPECIFIC EMBODIMENTS

Figure 1:
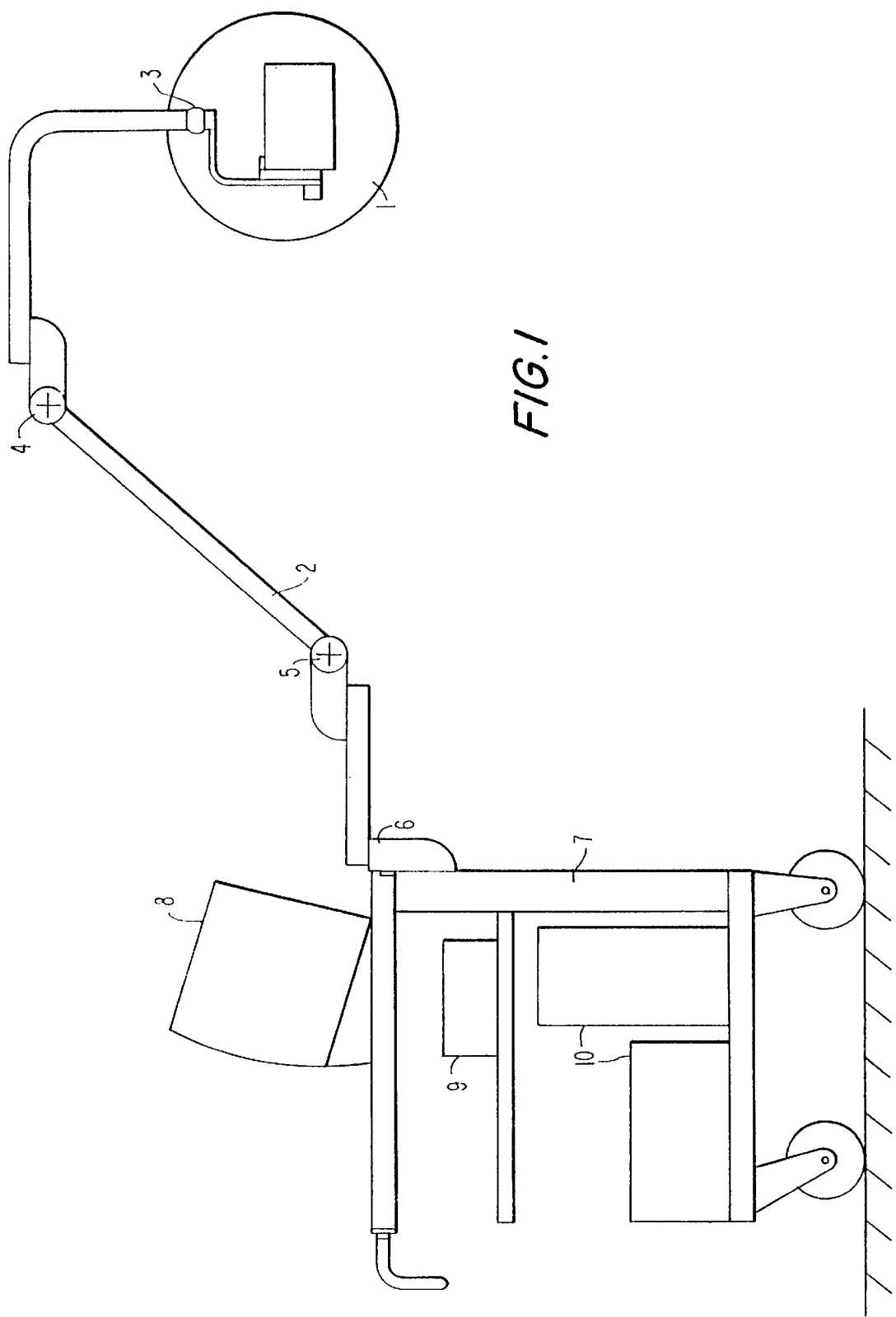
FIG. 1 is a schematic elevation of a light-weight mobile γ-camera assembly according to the invention.

The γ-camera assembly shown in FIG. 1 comprises a camera head 1 suspended from a foldable arm 2 comprising joints 3, 4 and 5 and pivoted at 6 to a trolley 7. Due to the three joints and the pivot of arm 2 the camera head 1 can be adjusted to the patient's body as may be required and may even reach the patient's chest from his leg side when he is in a lying position.

Trolley 7 carries an image display device 8, a computer 9 and the electronics 10 with analog and digital modules.

As shown in FIG. 1, the camera head 1 is suspended from arm 2 by means of a suspender member 11 linked at one end to arm joint 3 and at the other end to a joint 12 of the camera head. Joints 3 and 12 have a rotational degree of freedom of 360° each.

The camera head 1 comprises an array of four rows 13 of detector units 14, each unit comprising a detector plate with associated lead shielding marked together by numeral 15, and an associated collimator 16 clad with a lead shielding and having a quadrangular bore of uniform cross-sectional shape. The detector array is positioned on a carriage 17 which is slidably mounted on a crossbar 18 by means of cylindrical ball bearings 19 one of which is outwardly screw-threaded and engaged by a toothed wheel 20 keyed on a shaft 21 held in a bearing 22 and coupled at 23 to the shaft 24 of an electric servo motor 25.

Figure 2:
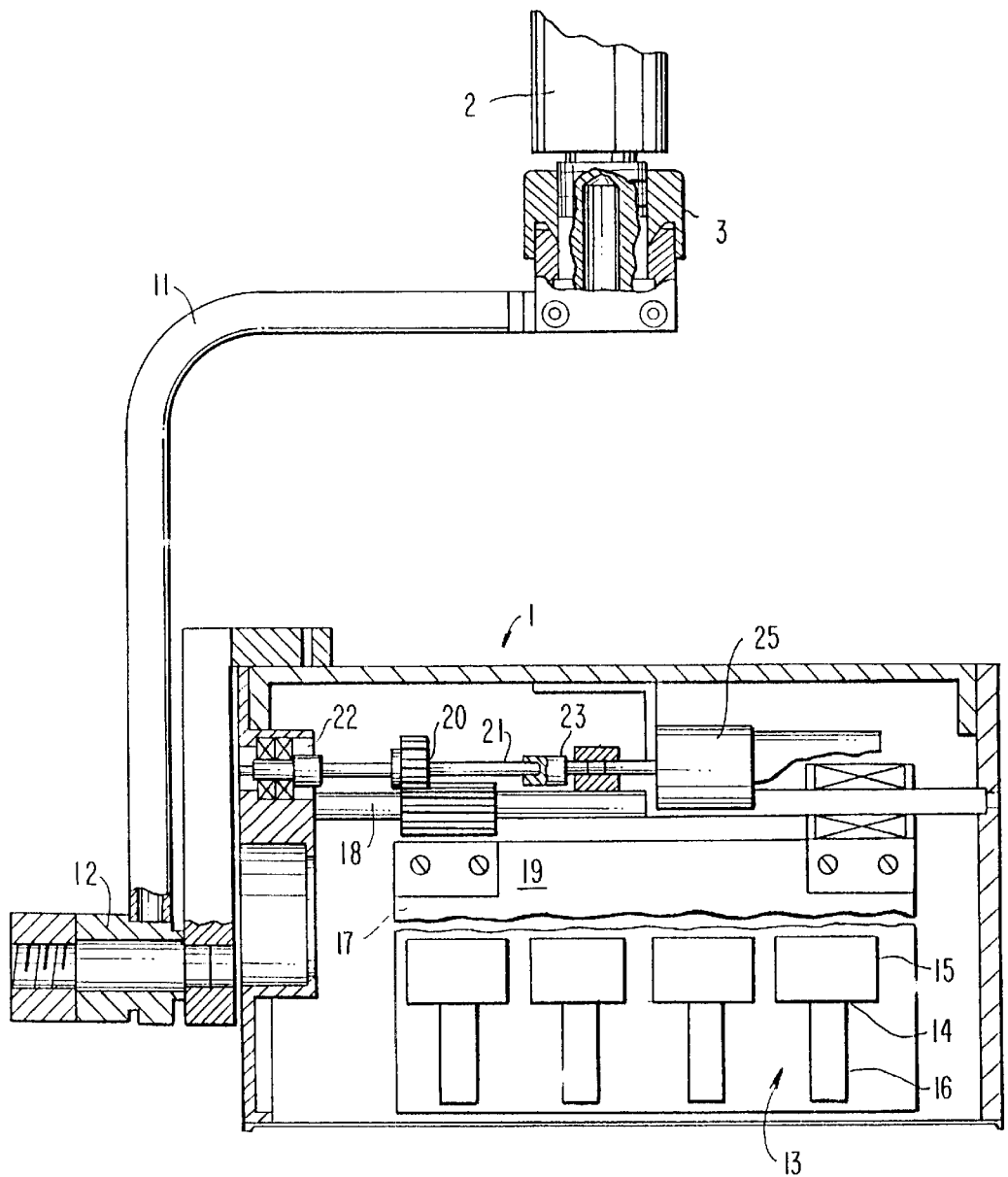
FIG. 2 is a section through the γ-camera head of the assembly of FIG. 1, drawn to a larger scale.
Figure 3:
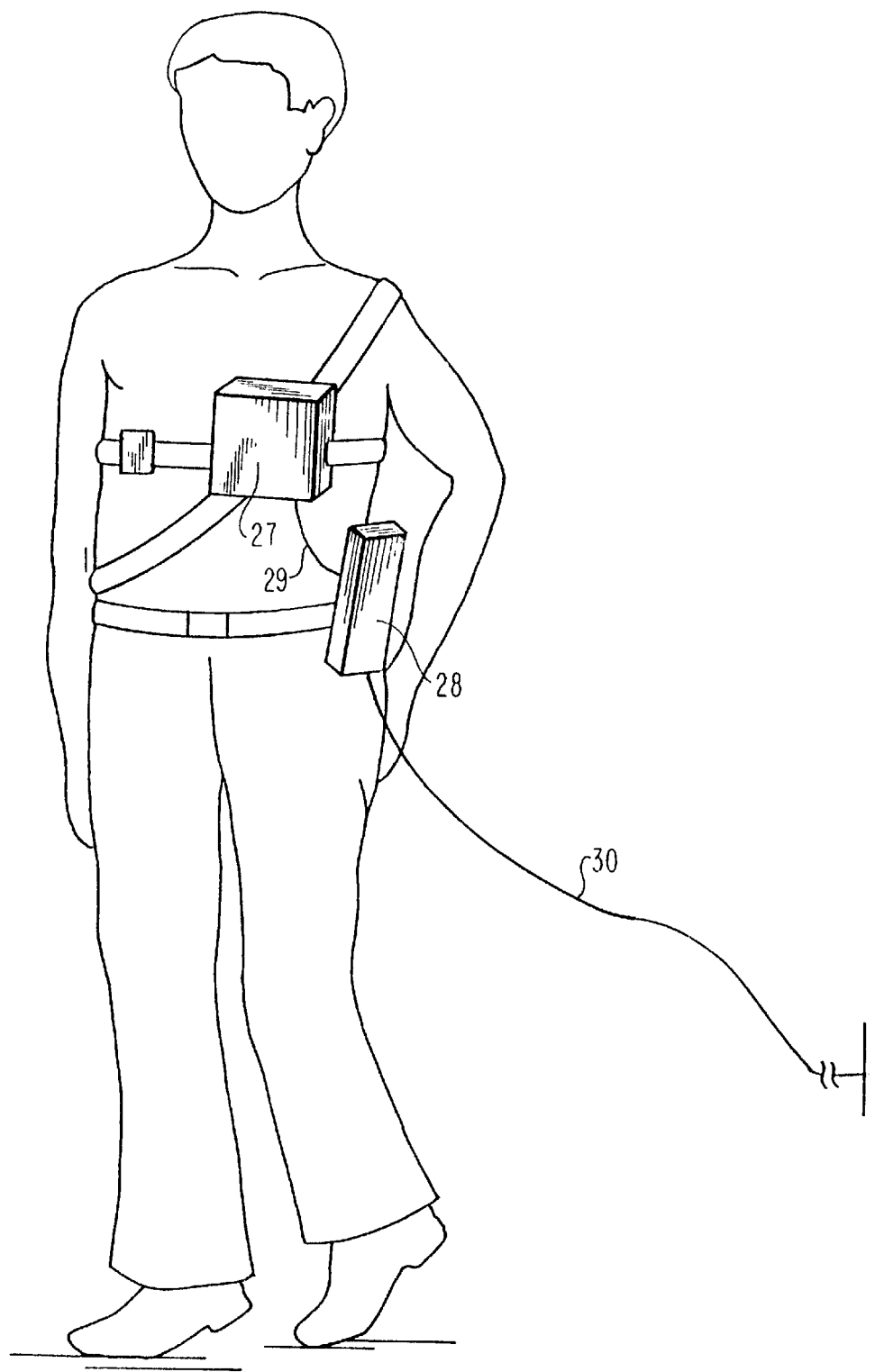
FIGS. 3 and 4 show a patient in the standing and sitting position, respectively, with attached camera head according to the invention in association with a data acquisition and storage device.
Figure 4:
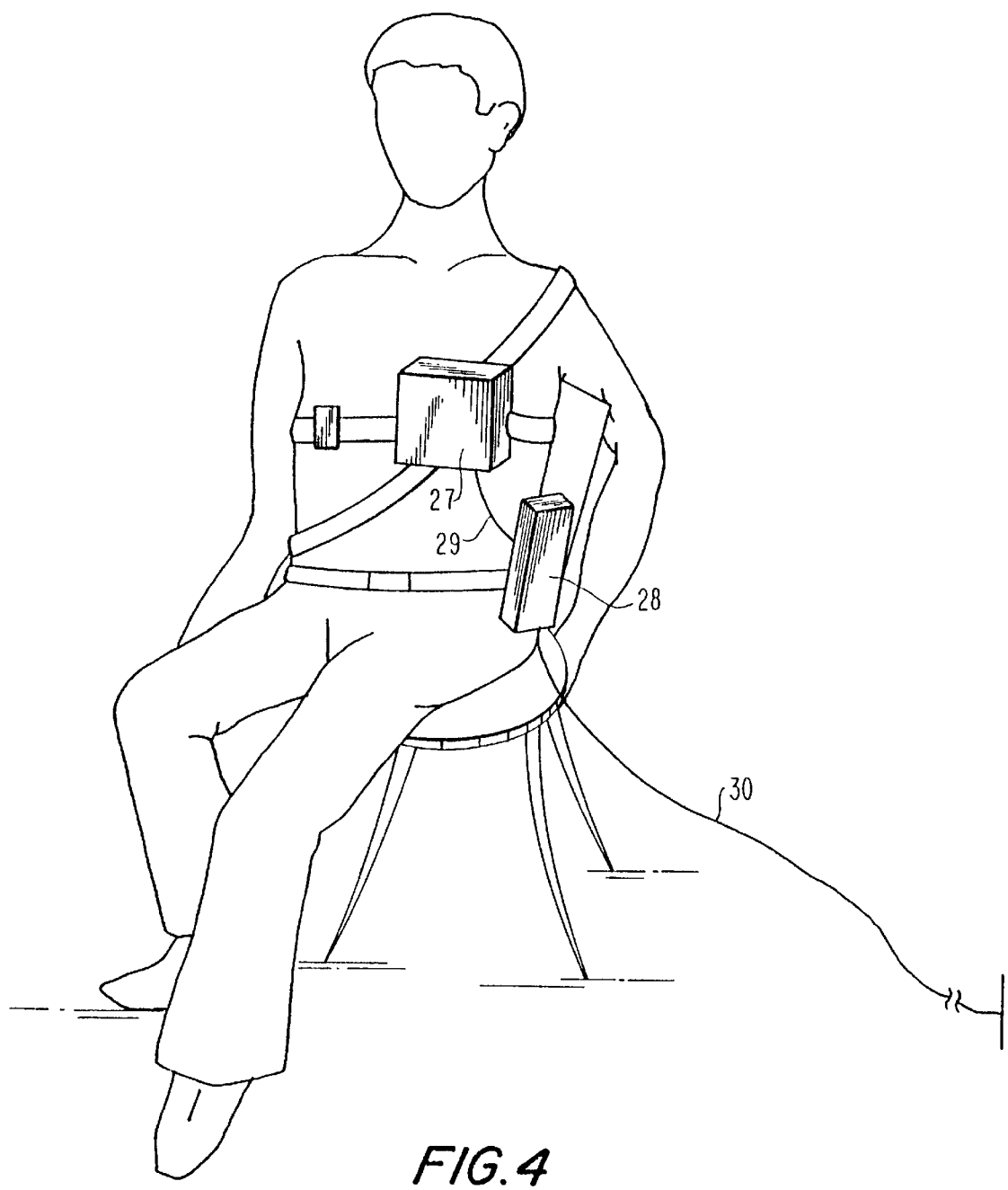

The embodiment of FIGS. 1 and 2 is suitable for wheeling inside the premises of a hospital or clinic. By another embodiment of the invention the camera head is a portable, detached unit attachable to the body of a patient who, if desired, may during the data acquisition continue with other functions. Such an embodiment is shown in FIGS. 3 and 4 in both of which a camera head 27 according to the invention is shown to be strapped to the chest of a patient who in FIG. 3 is shown standing and in FIG. 4 is sitting on a chair. Also attached to the body of the patient is a data acquisition and storage device 28 linked to the camera head 27 by means of a cord 29 which constitutes a communication link between the two. The data acquisition and storage device 28 is linked to a work station (not shown) via a cord 30. The work station may be in the vicinity of the patient in which case the linkage by means of cord 30 is direct. Alternatively, the work station may be remote in which case the communication link may be, for example, via a local area network (LAN) or a telephone line with the intermediary of a suitable transmitter device.

Figure 5:
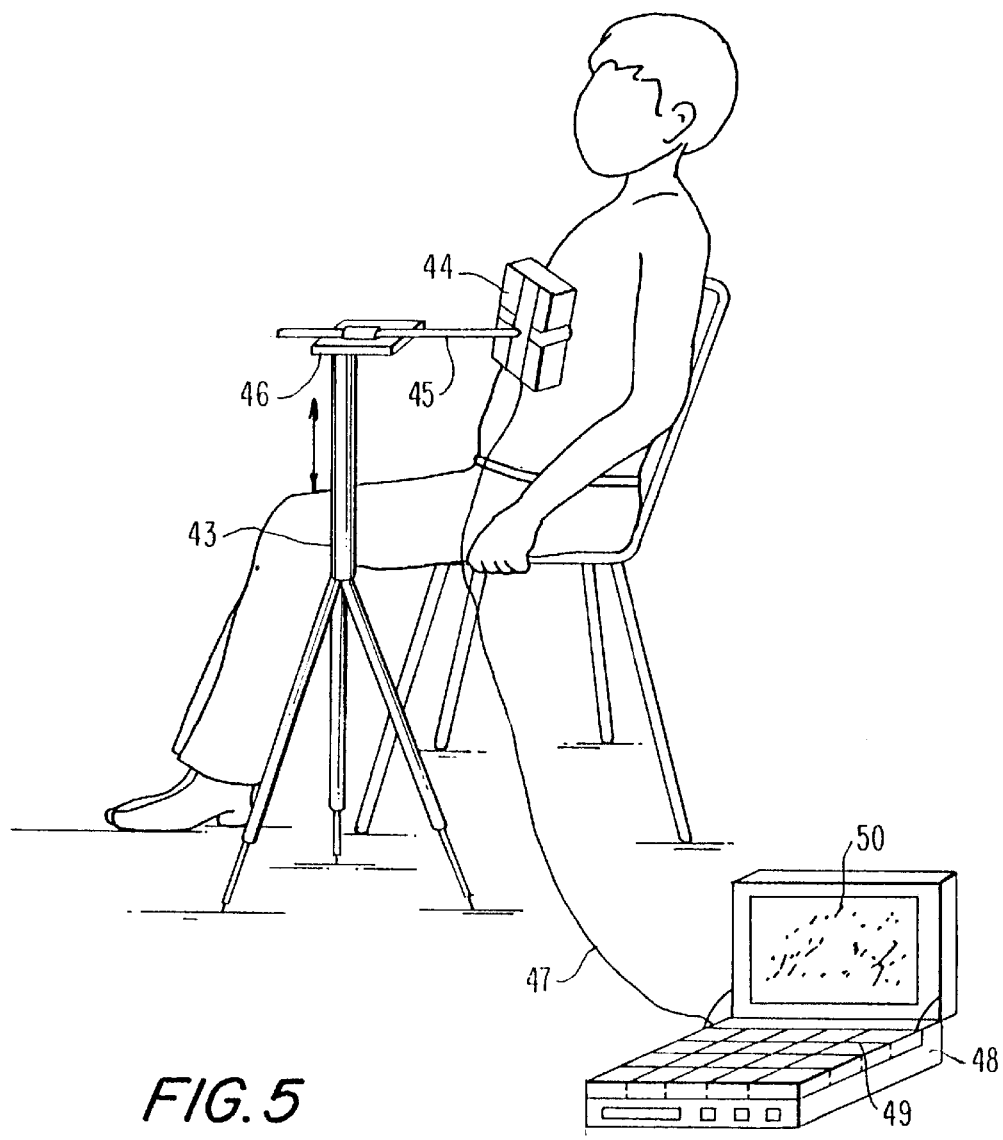
FIG. 5 shows diagrammatically a sitting patient with a positioned camera head forming part of a hand-carried γ-camera assembly according to the invention.
Figure 5A:
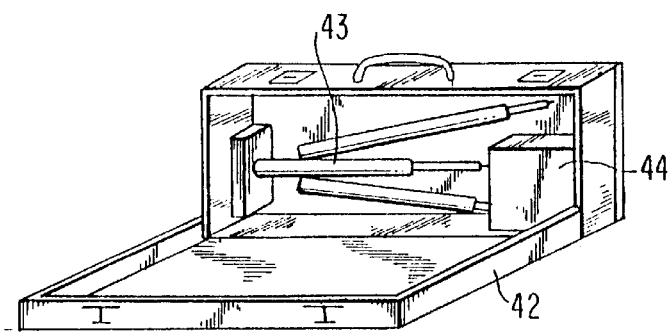
FIG. 5A shows an enlarged view of a bag for carrying the tripod and camera head of the gamma-camera assembly shown in FIG. 5.

Yet another embodiment of a camera assembly according to the invention is shown in FIGS. 5 and 5A. This embodiment in form of a fully hand-carried kit and comprises a first bag 42 storing a tripod 43 and a camera head 44. In operation tripod 43 and camera head 44 are withdrawn from case 42 and the camera head 44 is mounted by means of an arm 45 on the rotatable head portion 46 of tripod 43, proper positioning being effected by the adjustment of the positions of the tripod 43 and arm 45 thereon. The kit comprises a second bag 48 holding a lap-top computer 49 with display 50. In operation camera head 44 is linked to the lap-top computer 49 by means of a cord 47 serving as communication link.

Figure 6:
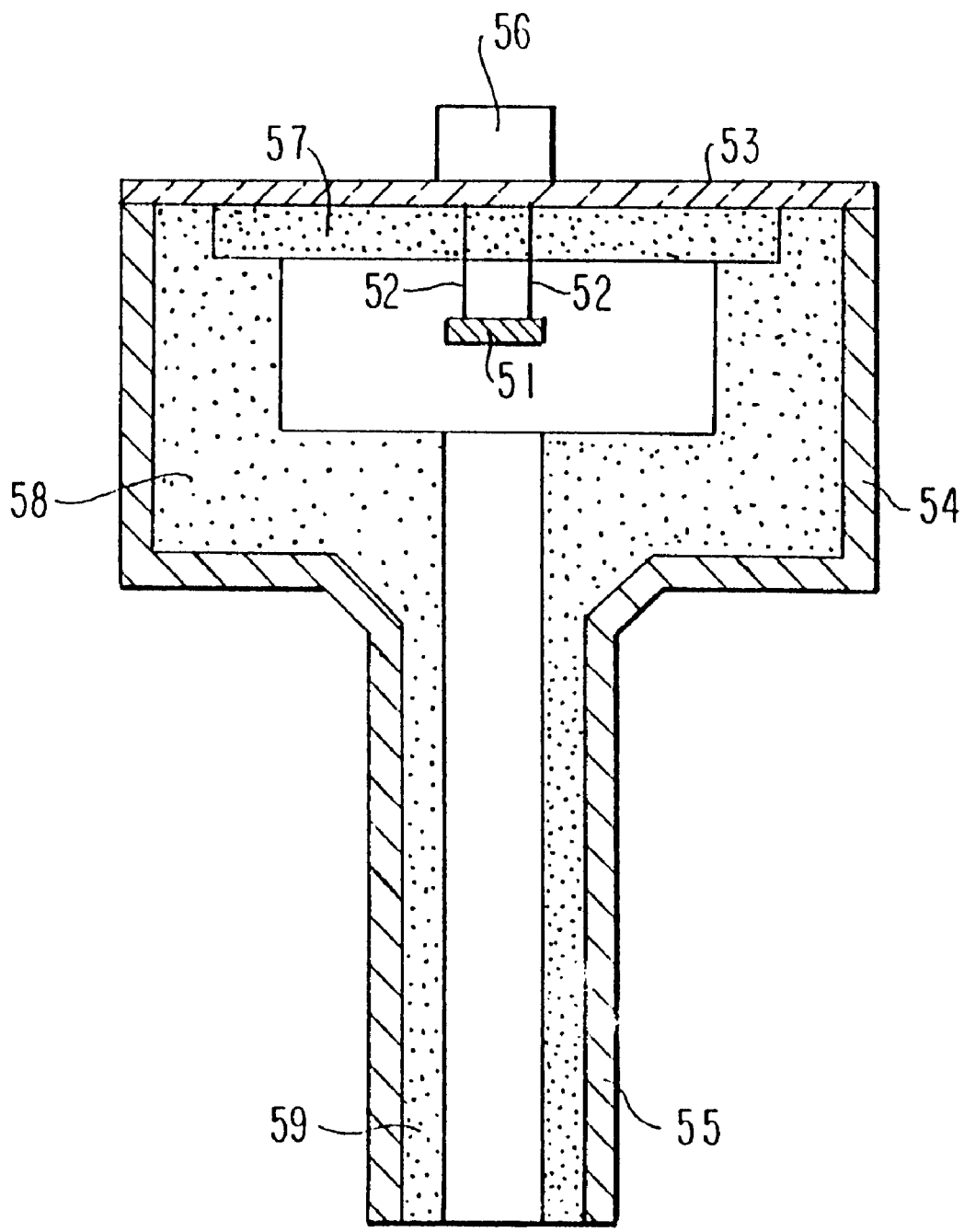
FIG. 6 is a section through one embodiment of a room temperature spectroscopy grade solid state detector unit with associated collimator used in a camera head according to the invention.
Figure 15:
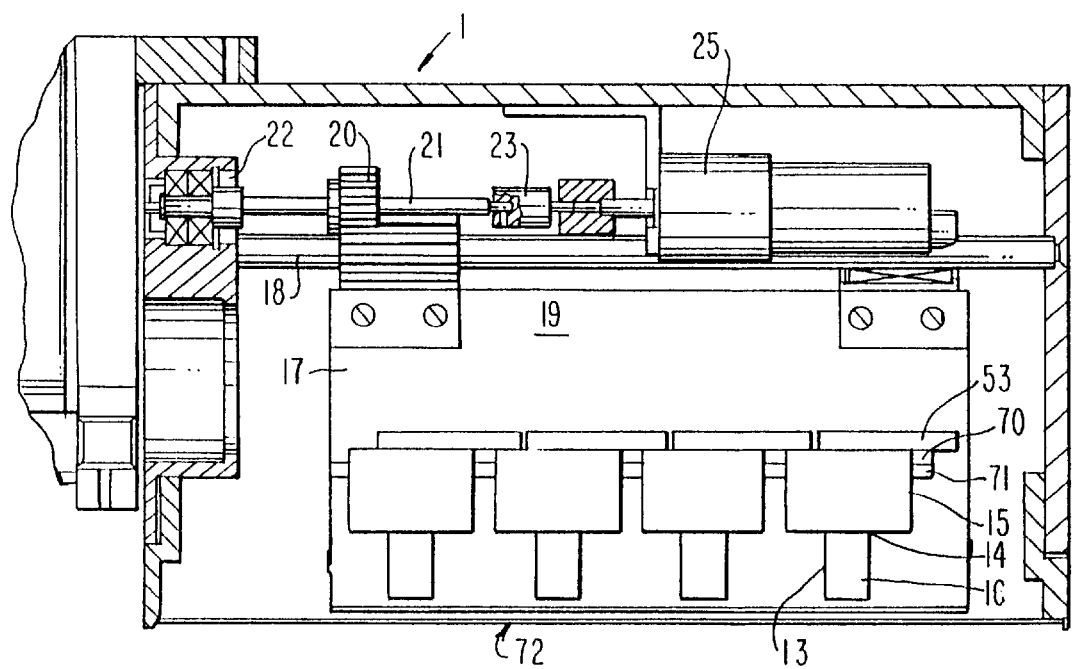
FIG. 15 is a section through an embodiment of a γ-camera head of the assembly which includes exchangeable collimators.

FIG. 6 shows a single detector unit forming part of a detector array in a γ-camera head according to the invention. As shown, the unit comprises a detector plate 51 mounted by means of conductor electrodes 52 on an electronic board 53 bearing on the backside a charge sensitive preamplifier 56. The detector plate 51 is located within the inner space of a casing 54 having a tubular collimator 55 of uniform quadrangular cross-sectional shape whose cross-sectional area is equal to the area of detector 51. Collimator 55 may be integral with casing 54 or alternatively be of an add-on type connectable to the casing in a firm fashion such as by screwing, or by a suitable catch mechanism 70, 71 as illustrated in FIG. 15. As shown therein, element 70 is a support for the electronic board 53 and the collimators 55 and element 71 is a hinge for supporting the collimators 55. Also, a dismantable cover 72 is required whereby different covers 72 enable different collimators 55 to be used. In this way each camera head may be fitted with two or more sets of exchangeable collimators for different needs.

Casing 54 holds a shielding lead plate 57 bearing on the electronic board 53, and a bell-shaped lead shield 58 merging into a quadrangular tubular portion 59 which clads the collimator tube 55 from within.

Due to the above compact design in which each detector is enclosed within a collimator, the γ-camera head according to the invention can be built to a minimum weight.

If desired, an additional add-on collimator may be mounted on collimator 55 for improvement of the spatial resolution.

Figure 7:
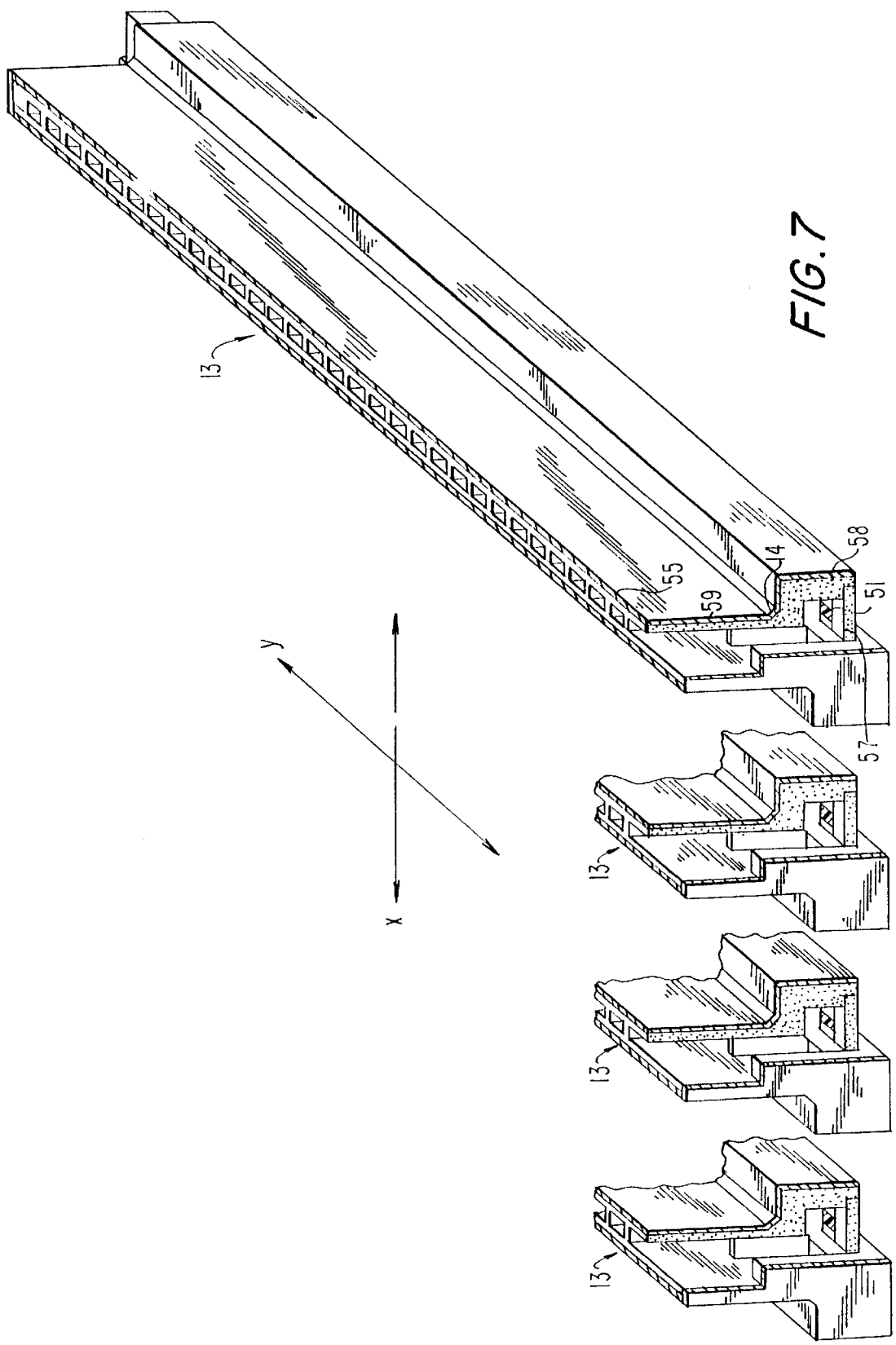
FIG. 7 is an axonometric view of a four-row array of room temperature spectroscopy grade solid state detectors and associated collimators in a camera head according to the invention.

The detector array in a camera head according to the invention is shown axonometrically in FIG. 7 in which the same numerals are used as in FIGS. 2 and 6. As shown, each detector row 13 holds a plurality of detector/collimator units 14 (see also FIG. 2) in each of which the collimator is either integral with the casing or is of an add-on type, and it is seen that the casing and collimator portions 54, 55 and the lead shielding 57, 58, 59 (see also FIG. 6) are in the form of a continuous matrix common to all detector units of one row.

Figure 16:
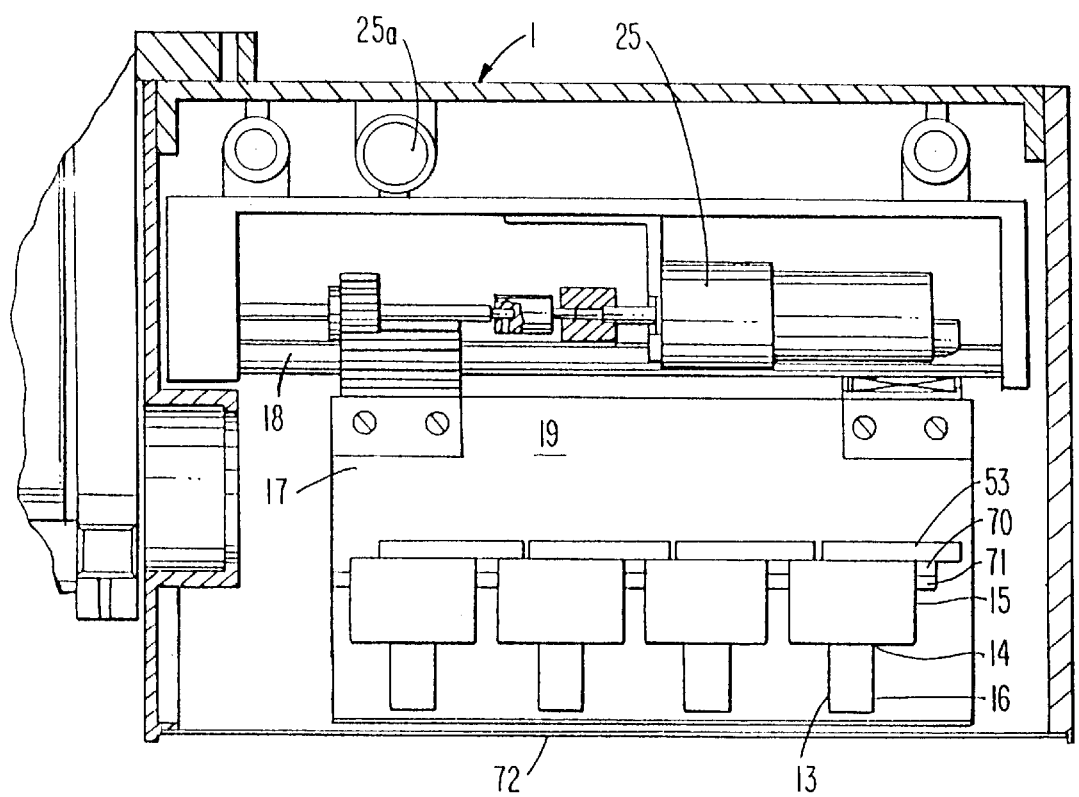
FIG. 16 is a section through an embodiment of a γ-camera head of the assembly which includes two separate motors.
Figure 17:
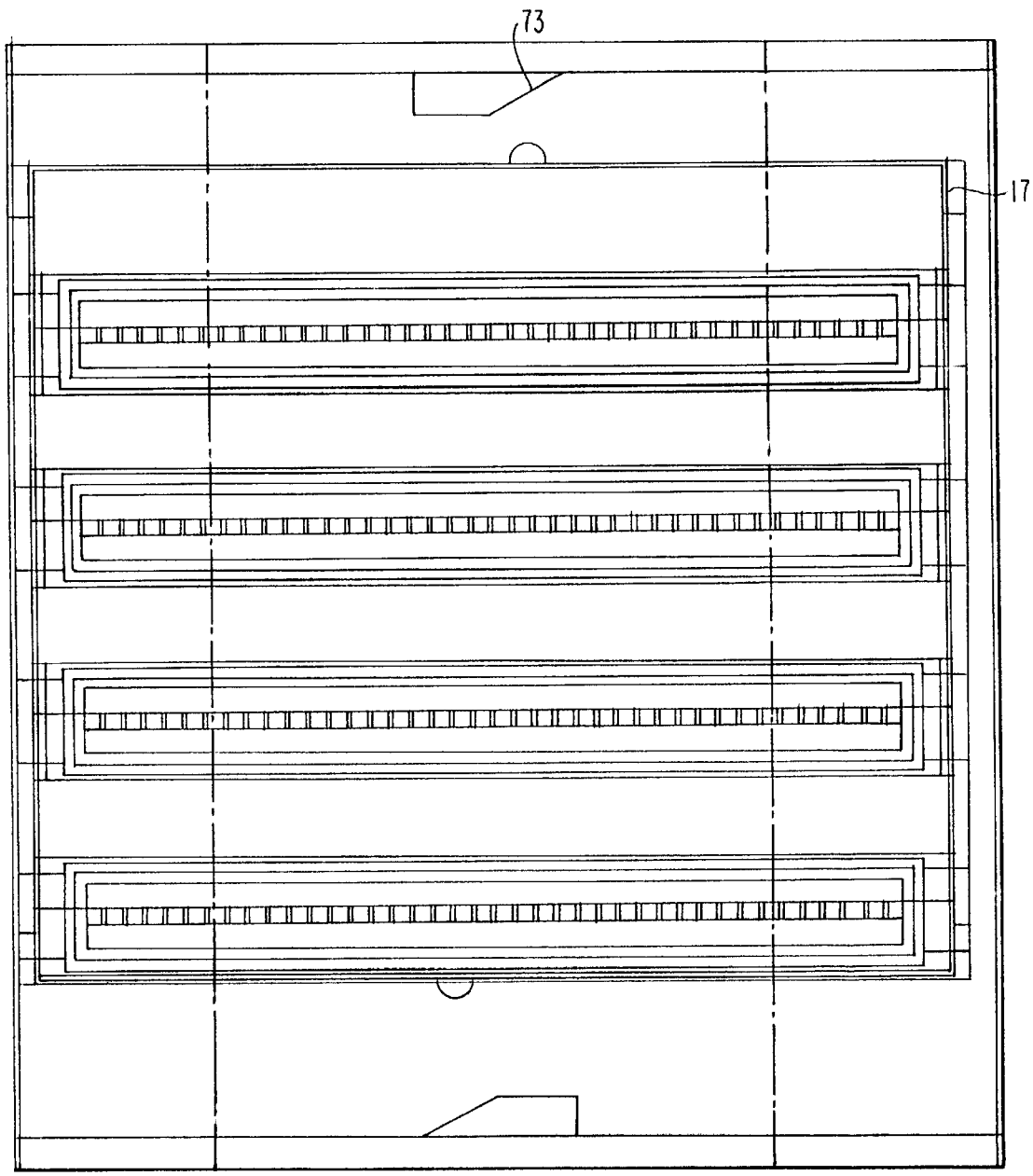
FIG. 17 is a diagrammatic plan view of a γ-camera head including a single motor for moving the detector assembly carriage bidirectionally.

As shown, the rows extend in a first, Y direction while their stepwise movement brought about by servo motor 25 (see FIG. 2) takes place in a second, X direction normal to the first, Y direction. If desired motor means may also be provided for the stepwise movement of the detector array in the first, Y direction. Such motor means may be in form of an additional servo motor, or else one and the same servo motor 25a as shown in FIG. 16; and may be designed for causing stepwise motion in both the X and Y directions, e.g., via means for translating the motion along the X axis to motion along the Y axis such a cam 73 having a slanting surface as shown in FIG. 17. In this manner, at the end of displacement along the X axis, the detector assembly is shifted by the slanting surface of cam 73 to a different position along the Y axis.

Figure 8:
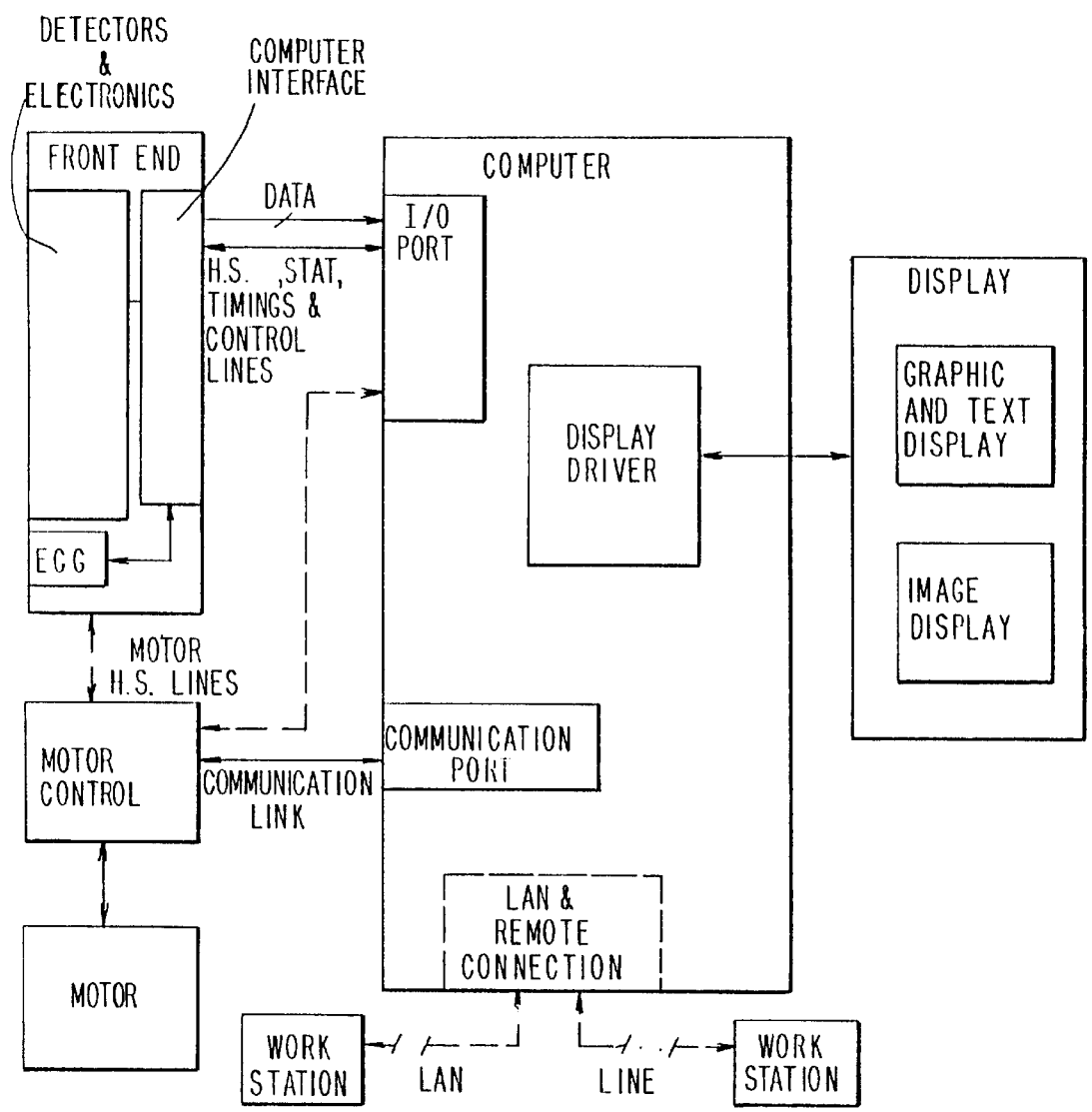
FIG. 8 is a block diagram of the hardware configuration in a γ-camera assembly according to the invention.

Attention is now directed to FIG. 8 which shows the hardware configuration of a γ-camera according to the invention. As shown, the hardware comprises a front end, a work station and a display module. The front end includes the detectors, an analog amplification system, a computer interface, an electro-cardiogram (ECG) input, a motor and a motor control. The work station comprises a computer with an IN/OUT (I/O) port for linkage to the computer interface of the front end, a display driver and a communication port. The display module has separate graphic text and image displays, on one or two separate screens.

Optionally the work station may be remote of the front end or else more than one work station and display module may be associated with one front end. In such cases the communication link between the front end and work station may be a LAN, a telephone line or any other suitable line, via a remote connection interface.

The communication links between the front end and the work station include several lines such as a data line which transfers data from the front end; a handshake (HS) line which controls the data transmission; a timing line which controls the ECG sampling; a motor control line; and status and control lines; all of which are connected to I/O port of the computer.

Figure 9:
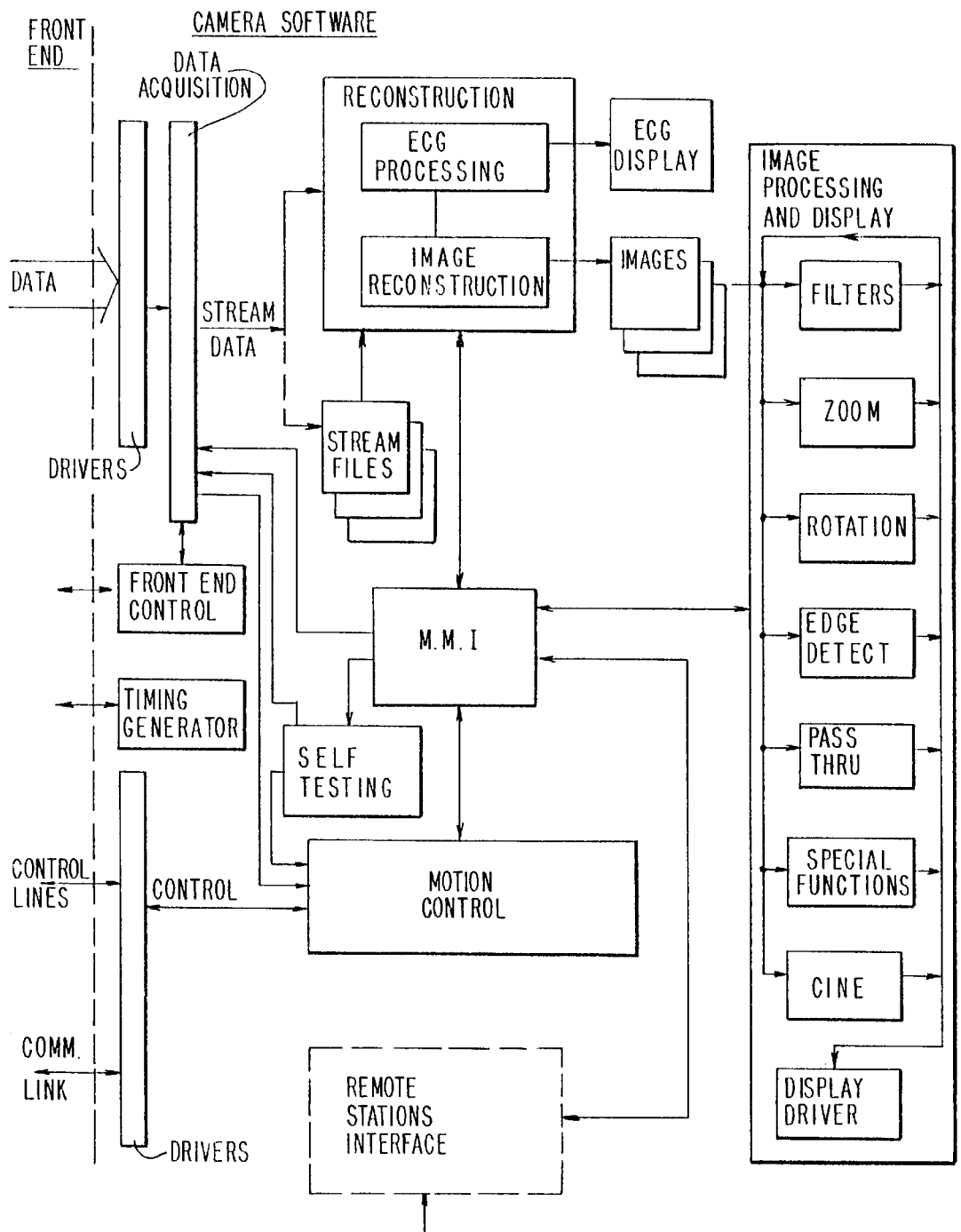
FIG. 9 is a block diagram of the associated software configuration.

Attention is now directed to FIG. 9 which shows the software configuration of the computer in FIG. 8. The software shown comprises:

a man/machine interface (MMI);
 a data acquisition and motion control module;
 an image processing and display module;
 a self-testing module;
 a remote stations interface module (optional).

The MMI controls all the system including data acquisition, motor control, image processing functions, system parameter functions and all the camera functions.

The data acquisition module receives the data from the front end, using the drivers, and converts them to a data stream which is fed to the reconstruction module. The data stream can be processed on-line or else be stored for later processing. If desired, both on-line processing and data storage may be practiced simultaneously.

During the data acquisition, the data acquisition module controls the front end and the motor control.

The reconstruction module comprises an ECG processing and an image reconstruction unit. The ECG processing unit analyzes the ECG signals and detects the R wave and it is used optionally when the camera is employed for multiple gated acquisitions, the ECG signals being displayed on the ECG display. The images reconstruction unit receive the acquired data and, where applicable also the R wave timing, and generates either several images in an ECG rated acquisition or one single image in an ungated acquisition.

The images are transferred to the image processing and display module in which each image passes several types of transformation such as filtering, zooming, rotation, edge detection, special functions for the camera applications and display driver. The images can be displayed separately or in a motion display by means of the cine, either on-line or upon processing of stored data.

In order to give the user the option of receiving and processing data at a remote work station there is provided a remote stations interface module for connecting the camera to other stations via suitable communication links such as local area network (LAN), a telephone line and the like.

In operation the detector array shown in FIGS. 2 and 7 is moved stepwise in the second, X direction, the rise of each step depending on the size of the individual detectors and being sufficiently small so to produce a continuous image. Assuming the overall area that a camera head according to the invention can cover to be 16×16 cm$^2$, the number of detectors in each row to be 32 and the number of rows to be 4, the area of 16×16 cm$^2$ is divided into 78×64 pixels. Assuming further that each detector has the size of 4×4×2 mm$^3$ and the space between two adjacent rows is 38 mm, then for passing all pixels the individual steps will be of the order of 2.0 mm.

If desired, the detector array may additionally be moved stepwise in the first, Y direction with each step being, for example, half of the detector size in the Y direction. In such an embodiment either another servo motor (not shown) will have to be provided or else a single servo motor is used with capability of stepwise shifting the array of detectors in both the X and Y directions.

Figure 10:
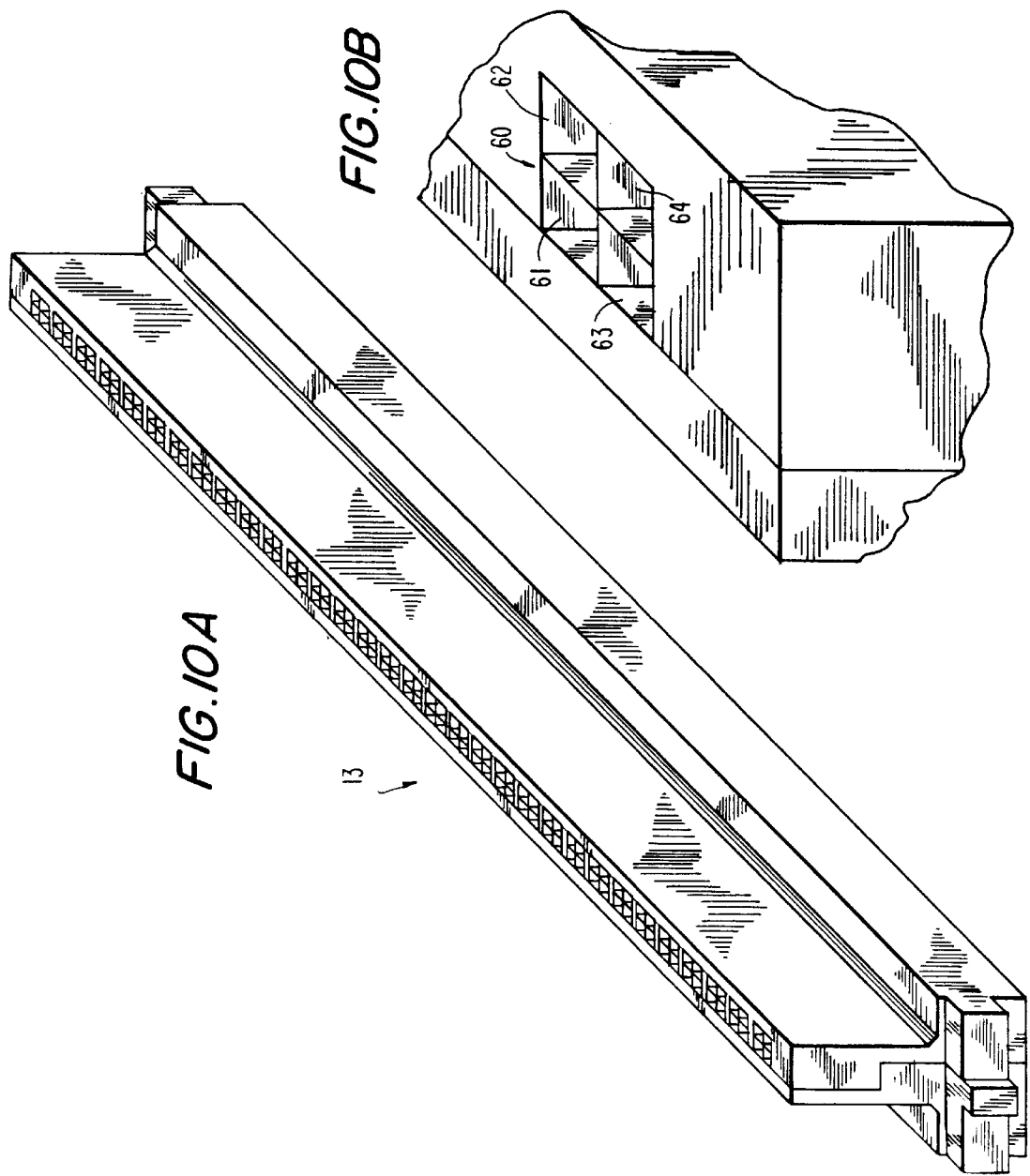
FIG. 10A is an axonometric view of an array constituting row of room temperature spectroscopy grade solid state detectors and associated collimator for use in a camera head according to the invention, wherein each detector/collimator unit is made in accordance with another embodiment.
FIG. 10B is an enlarged view of a section of the array shown in FIG. 10A.

In the embodiment of FIGS. 10 and 10A each detector plate in a detector row 13, such as plate 51 in FIGS. 6 and 7, is associated with a multiple channel collimator 60 having four parallel channels 61, 62, 63, 64. The total cross-sectional area of channel 60 is equal to that of the detector. With a multiple channel collimator detector unit it is possible to achieve the same solid angle as with a single channel collimator detector unit of the kind shown in FIGS. 6 and 7, with, however, a shorter collimator length, whereby the weight of the γ-camera head according to the invention is further reduced.

Figure 11:
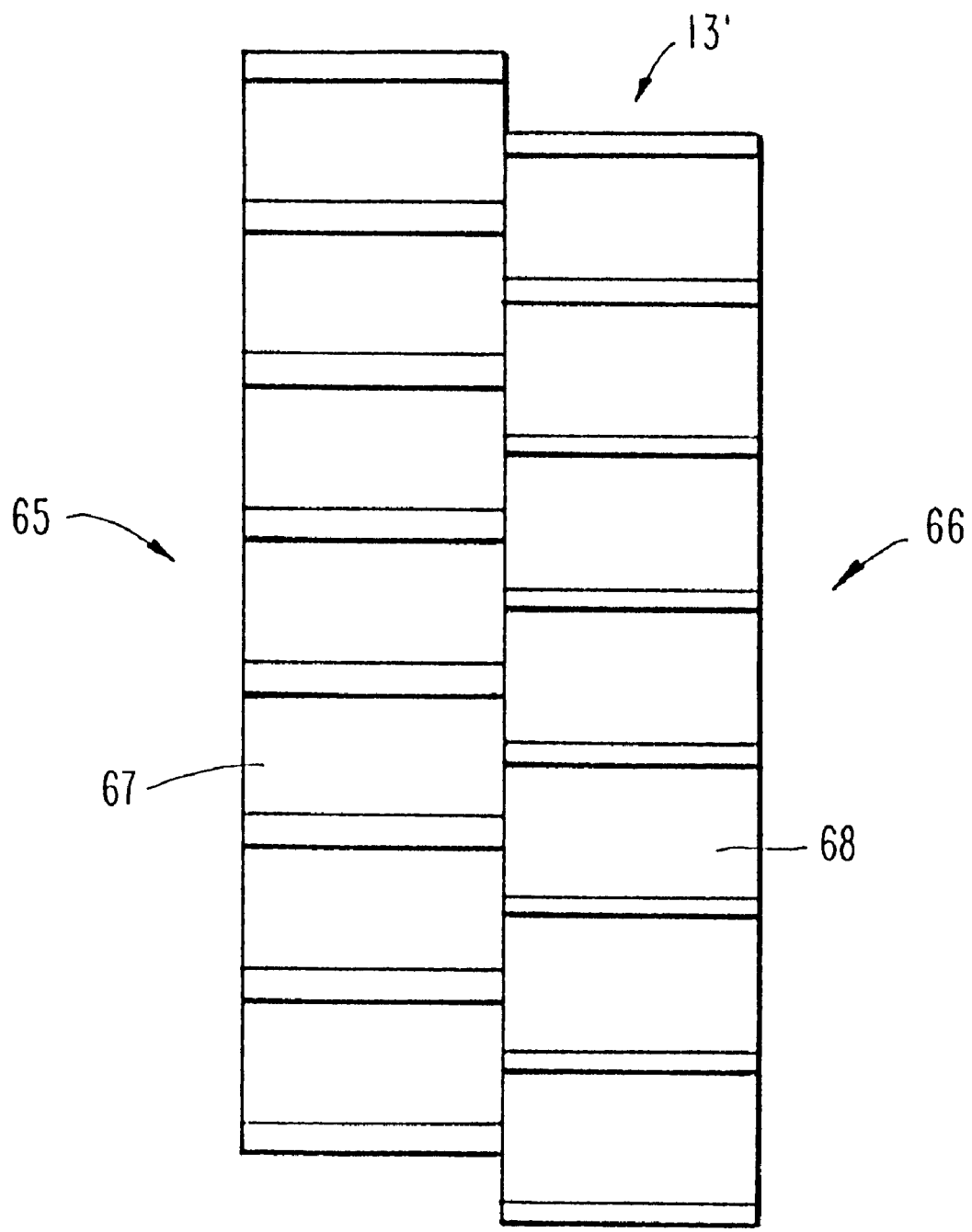
FIG. 11 is a diagrammatic plan view of an assembly of two juxtaposed, mutually staggered rows of solid state detector units with associated collimators for use in a camera head according to the invention.

In the embodiment of FIG. 11 two detector rows 65, 66 are juxtaposed and staggered, forming together a detector row assembly 13'. Each detector unit 67 in row 65 is shifted relative to an adjacent unit 68 in row 66 by half the dimension of a unit in the Y direction, i.e. by half the distance between the centers of two adjacent detector units.

If desired, an assembly 13' may comprise three rows and in that case the stagger between the juxtaposed rows will be one third of the dimension of a unit in the Y direction.

With such embodiments a step-wise movement of the detector array in the Y direction may not be required.

The electronics in the camera head consists of hybridized charge sensitive preamplifiers directly connected to the CdTe detectors. The detectors are biased to about 100 V. The sensitivity of each low noise, charge sensitive preamplifier is 1V/pC and the equivalent noise charge is equivalent to 300 electrons. This low noise preamplifier which is mounted very close to the detector enables to obtain good energy resolution. The preamplifier has also a test input which is fed parallel to all channels and enables to check the electronic analog and logic circuitry and to equalize the gain of all channels.

Each charge sensitive preamplifier is connected to an amplifier-shaper. The coarse gain of each amplifier is suitably selected, say 1000, and the fine gain is externally adjustable, e.g. by a factor of 2, in order to equate the gains of all channels. The output pulses from the amplifier-shaper has a Gaussian shape, a 2 µsec full width at half-maximum (FWHM).

In accordance with one embodiment of a γ-camera assembly according to the invention, analog amplifiers are located at the working station detached from the camera head and suitably connected to the charge sensitive preamplifiers in the camera head.

In accordance with another embodiment hybrid preamplifier/amplifier modules are located within the camera's head.

In accordance with yet another embodiment, the charge sensitive preamplification means associated with each detector is an application specific integrated circuit (ASIC).

If desired, charge sensitive preamplification means may be integrated within each detector.

The outputs of the analog channels are connected to an analog-to-digital converter (ADC), e.g. an 8 or 12 bit ADC. If ASIC technology is used, it is convenient to have a separate analog circuitry for each detector and in such a case multiplexing is performed simultaneously on all detectors using a logic circuit which scans the data residing in a memory buffer.

If desired, a group of amplifiers may be connected to the same analog-to-digital converter with the use of multiplexing, identification of the detector being carried out by a trigger signal derived from each amplifier.

A group of preamplifiers may also be connected to the same amplifier and the same analog-to-digital converter with the use of analog multiplexing, identification of the detector being again carried out by a trigger signal derived from each preamplifier.

The digital data of the ADC is routed event by event into a first in, first out (FIFO) memory. For each event two types of information are routed: the digital output of the ADC, which corresponds to the energy of the event, and an address, e.g. 8 bit, which indicates the identity of the detector within the matrix which has transmitted the signal. The counts per step for a given detector are accumulated in a predetermined energy window.

Where a γ-camera assembly according to the invention is associated with an ECG, the ECG output is connected to an ADC, e.g. 8 bit, and the ECG signal is routed periodically to a FIFO memory, say every five milliseconds. The ECG signals are analyzed for peak detection in order to locate the R wave. Having the timing of the R wave, analog signals are divided into time slots within the heartbeat. The interrupts which occur every five milliseconds and the data transfer to the memory of the computer is routed via an I/O card.

The acquired data are transformed into one image or a sequence of images. For ungated acquisition the total counts acquired during each step by each detector are displayed after normalization to equalize the efficiency for all detectors.

For ECG gated acquisitions the data are divided into time slices, say 16, corresponding to different phases of the heartbeat. In other words, for each step (X) there are 16 time frame images each containing the total number of counts of a given detector row (Y). The 16 time images are displayed separately or may be displayed in a cine pattern, where the first frame, for instance, represents the image at the end of a diastole.

X-rays and γ-rays emitted from the organ are aligned and reach the detectors from a solid angle defined by the collimator, e.g. in parallel flux in the case of the uniform rectangular collimators shown in FIGS. 6 and 7. The x-rays and γ-rays interact with the detectors via photoelectric and Compton scattering. At energies up to 180 keV the photoelectric effect dominates. The amount of charge created in the detector depends on the energy deposited, the energy required to create an electron-hole pair being 4.43 eV in case of a CdTe detector.

In the embodiment here shown the septum forming lead shielding between the collimator bores in a detector row is assumed to be 1 mm thick. Depending on requirements, the thickness of the lead shielding may be reduced to say about 0.5 mm.

Figure 12:
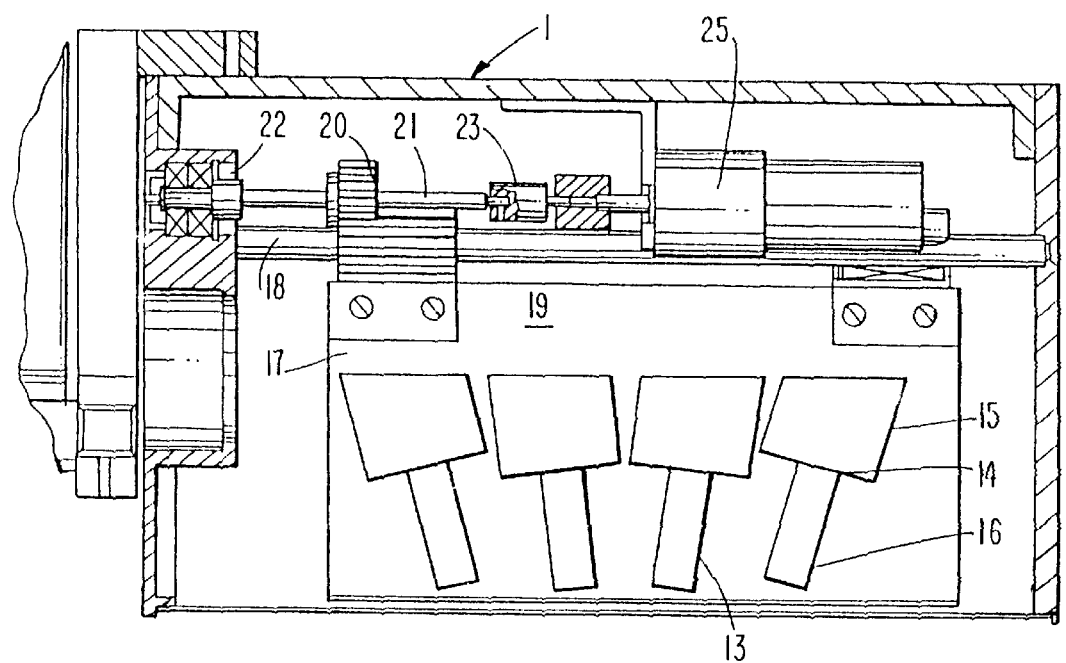
FIG. 12 is a section through an embodiment of a γ-camera head in which the collimators in the parallel rows are converging in both the first and second directions and thereby designed for the interception of convergingly propagating γ-radiation.
Figure 13:
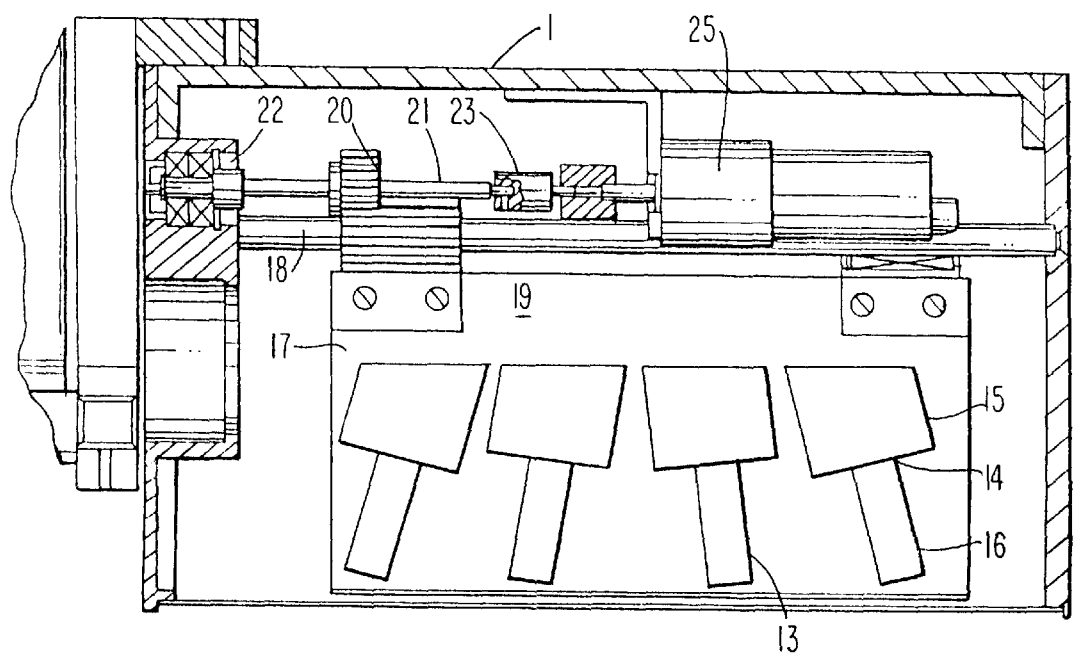
FIG. 13 is a section through an embodiment of a γ-camera head in which the collimators in the parallel rows are diverging in both the first and second directions and thereby designed for the interception of divergingly propagating γ-radiation.
Figure 14:
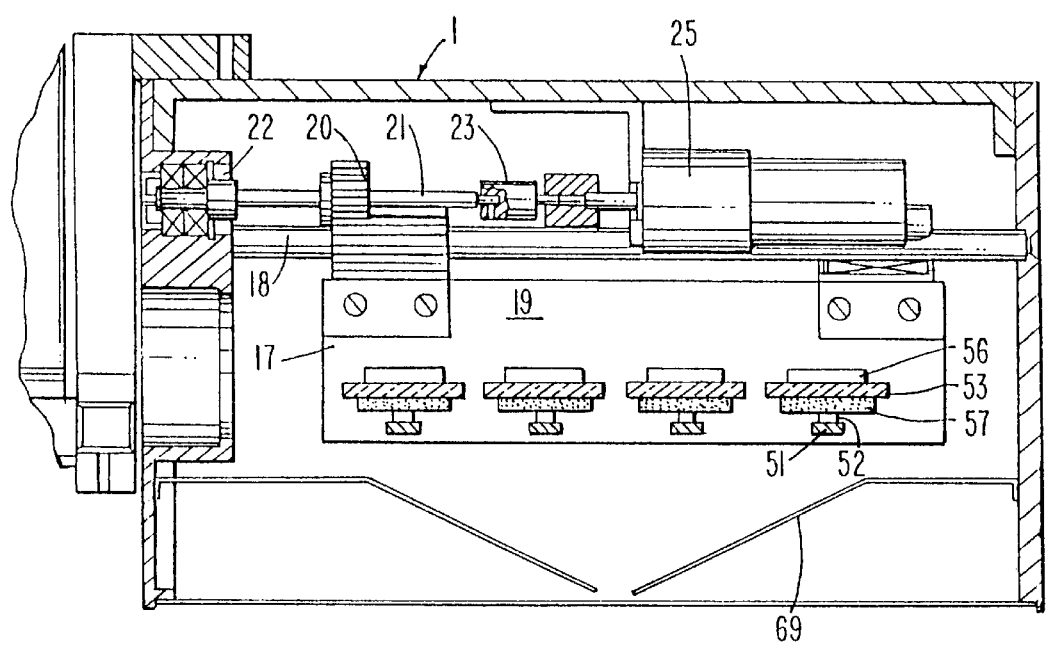
FIG. 14 is a section through the γ-camera head of the assembly which shows a single pinhole collimator common to all detectors and which covers the entire field of view.

Furthermore, if desired the parallel flux geometry of the collimators shown in FIG. 2, i.e. the uniform tubular design thereof, may be replaced by converging, diverging or pinhole geometries as shown in FIGS. 12, 13 and 14, respectively. In FIG. 14 the pinhole collimator is designated by reference numeral 69.

Thus, FIG. 12 shows a γ-camera head in distinction from the γ-camera head shown in FIG. 2 in that the rows of detector units 14 are converging in the second direction to be adapted for the interception of convergingly propagating oncoming γ-radiation. In FIG. 13, on the other hand, rows 13 of detectors 14 are diverging in the second direction to be adapted for the interception of divergingly propagating oncoming γ-radiation. In the embodiment shown in FIG. 14, individual collimators 55 in the detector units shown in FIG. 6 are replaced by a pinhole detector or collimator 69 common to all of the detector plates 51. If desired, there may be several pinhole collimators aligned in at least one row extending in the first direction.

The electric servo motor in a γ-camera head according to the invention is light weight and of a small size and is associated with an encoder and a suitable transmission, e.g. a 1:25 gear. It is connected to a controller and enables the movement of the camera head in predetermined steps in one direction. If desired it is possible to use a state of the art modified motor which will enable to move the detector array in both the X and Y direction so as to improve resolution in the Y direction.

FIG. 15 shows a gamma-camera head according to the invention in which each collimator unit 14–16 is made separate of the detection plate 51 and electronics 53 (FIG. 6 in the main patent) and are of the add-on type connectable to the casing via suitable connector means, e.g. hinges 71 mounted on supports or bearings 70 (only one of which is shown). In this way each camera head may be fitted with two or more sets of exchangeable collimator units designed for different needs.

The use of room temperature solid state spectroscopy grade detectors such as CdTe, CdZnTe, $PbI_2$ or $HgI_2$ detectors enables to achieve a good intrinsic spatial resolution limited only by the actual size of the individual detector and independent of the incident photon energy. Very good image quality is obtained in a wide range of energy, from 20–180 keV. The multi detector nature of the γ-camera head according to the invention, which is the result of the array of solid state detectors, and the detector/electronics combination enable high count rates of about $10^6$ counts/sec/total detector area.

Due to its small size and light weight the camera head of a γ-camera according to the invention can be brought to the patient and be readily attached to any desired body part. Moreover, the small, lightweight γ-camera is well adapted for inclusion in a single photon emission computer tomography (SPECT) configuration, or to any other stationary γ-camera configuration.

Figure 18:
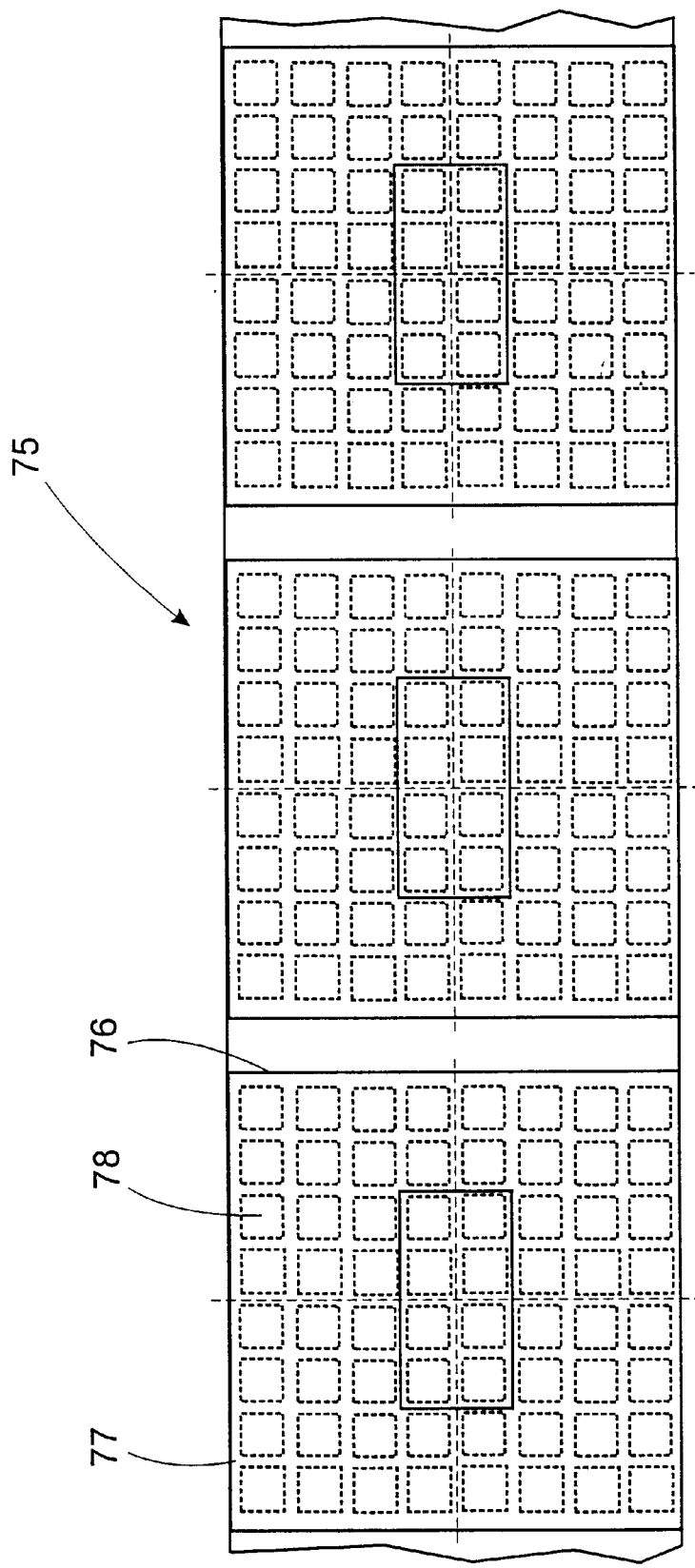
FIG. 18 is a plan view of an array constituting row in a detector assembly of γ-camera head according to the invention.
Figure 19:
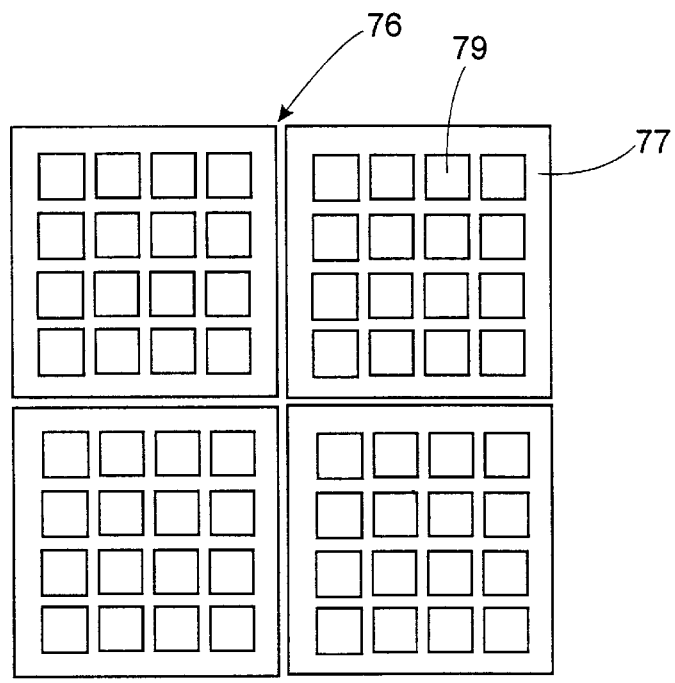
FIG. 19 is a plan view of a detection unit holding four monolithic detector arrays.
Figure 20:
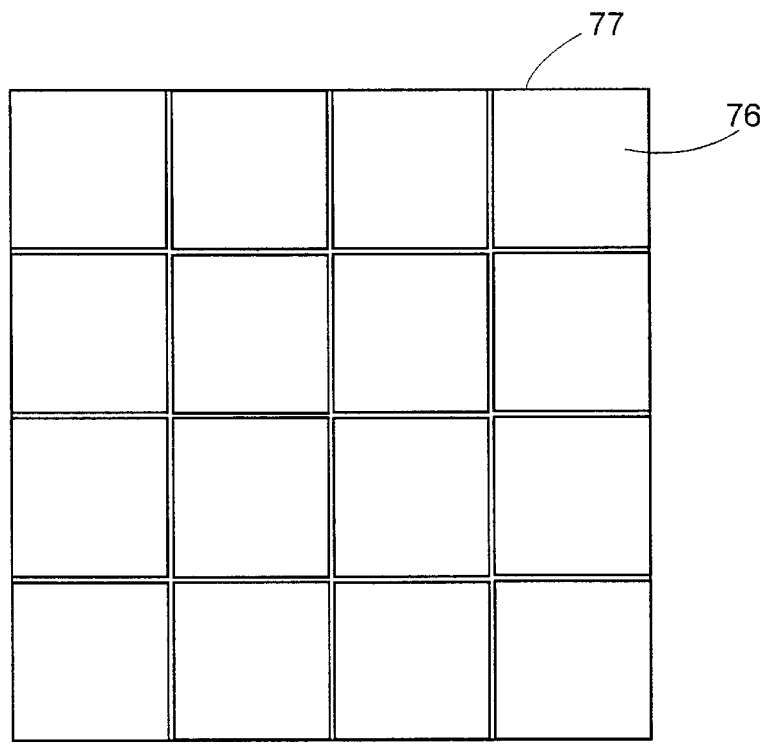
FIG. 20 is a plan view of a single monolithic detector array holding sixteen pad detection elements.

A preferred embodiment of an array forming detector row in a detector assembly of a gamma cover head according to the invention is illustrated in FIG. 18 and some details are shown in FIGS. 19 and 20. As shown, each row 75 comprises a plurality of detector units 76 each composed of four monolithic detector arrays 77 having on its top side means 78 for connection to an Application Specific Integrated Circuit (ASIC). As shown, each monolithic detector array 77 comprises 16 pad detection elements 79. As shown, lengthwise the monolithic detector arrays are arranged in two parallel alignments.

A γ-camera head according to the invention may, for example, hold an array of 12 rows 75 of FIG. 18 adjacent to each other, each row containing, for example, 48 monolithic arrays of spectroscopy grade solid state detectors gathered as 12 detector units. The number of monolithic arrays in a detection unit depends on both maintenance requirement and the ASIC electronic configuration. Each monolithic array is a segmented readout detection element of 16 pads with each pad serving as a pixel in the imaging system. Thus, in the foregoing specific example a total of 576 monolithic arrays or 144 detection units form a two-dimensional array of detectors covering the entire field of view. In this example, each detector unit holds a total of 64 pad detection elements each of which is connected to a low noise preamplifier of a common ASIC. In other words, each self-triggered ASIC supports 64 pad detectors and contains the preamplification, amplification-shaping and the encoding of the pad detection elements each of which is triggered separately by a gamma interaction. The ASIC electronics also contain as an option means to correct the total created charge in the pad detection elements for incomplete collection of holes due to trapping.

Figure 21:
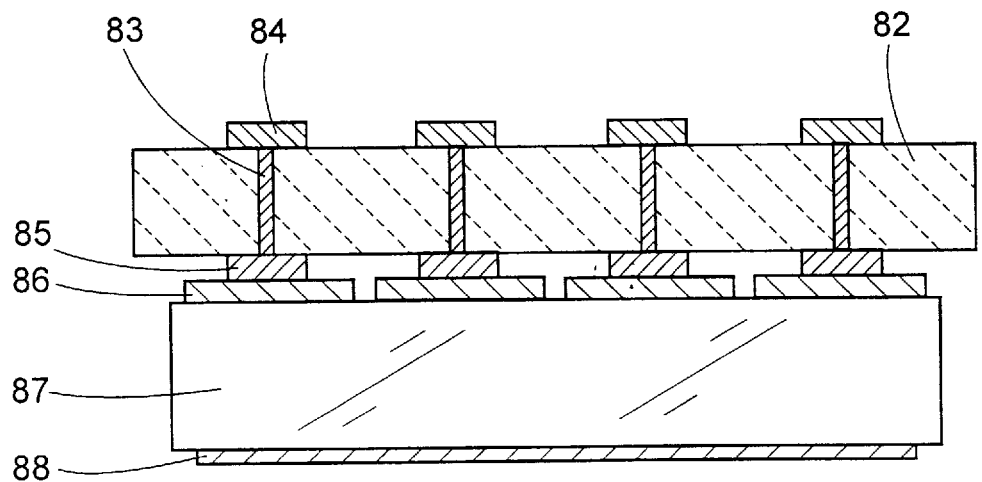
FIG. 21 is a schematic cross-sectional view of a square monolithic detector array holding sixteen pad detection elements.

Monolithic detector arrays are known per se and do not form part of the present invention. Briefly, and as shown in FIG. 21, such array comprises a ceramic base body 82 fitted with a plurality of first electrodes 83 having each an upper terminal plate 84 for connection to the ASIC and a lower terminal plate 85 bearing on an associated detector pad 86 secured to the rear face of a solid state room temperature detector crystal 87 bearing on its top face a metal plate 88, applied, for example, by vapor deposition and serving a second electrode common to all detector pads 86. All electrodes 83 are connected to the ASIC. Preferably, the segmented electrodes 83 are put at a positive potential and the common electrode 87 at a negative potential, whereby the gamma radiation impinges the negative electrodes of the detection unit which yields better charge collection and energy resolution of the monolithic array than if the radiation were to impinge the positive electrode. The energy absorbed in the region between the common electrode and the pad detection element in the form of electron/hole pairs is transferred to a voltage signal by the ASIC. The electrons are drifted into a pad electrode.

Figure 22:
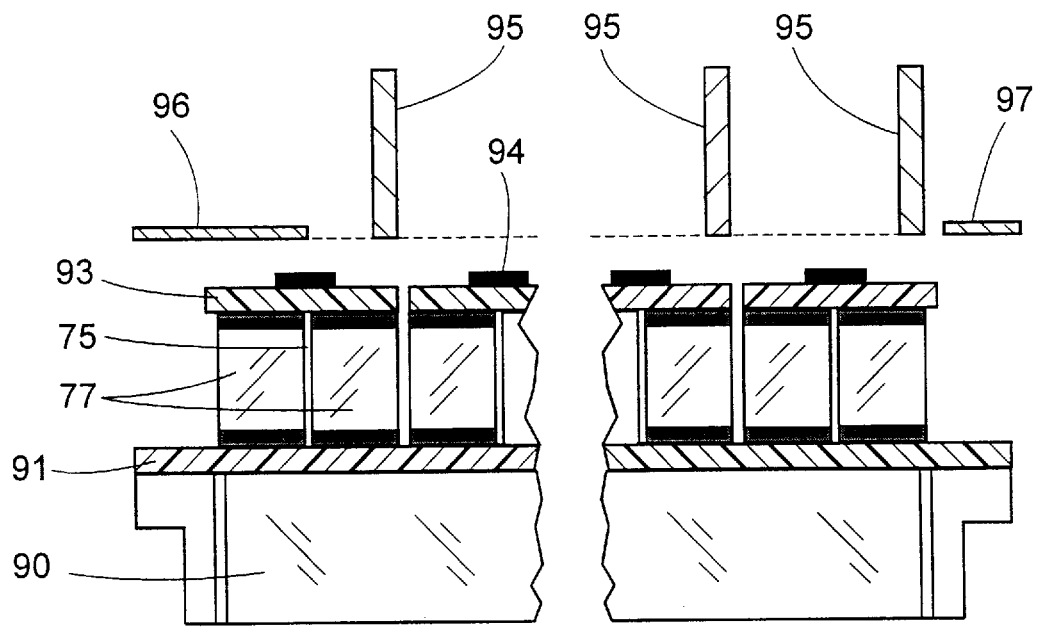
FIG. 22 is a schematic cross-section view of γ-camera head according to the invention.

A γ-camera head according to the invention having an array of detector rows of the kind shown in FIG. 18 is diagrammatically illustrated in FIG. 22. As shown, it comprises a collimator unit 90, a high voltage printed circuit board (PCB) 91 common to the overall camera head, a plurality of detector rows 75 each comprising a plurality, say 12 detector units 76 holding each four monolithic detector arrays 77 (sec FIGS. 18 and 19). The high voltage PCB 91 comprises flexible strips (not shown) two for each row in association with the two alignments of monolithic detector arrays, which ensure full contact with all electrode terminal plates 88 thereof (see FIG. 21). There are further provided twelve detector/ASIC PCBs 93, one in association with each row 75, each fitted with an ASIC 94, each ASIC 94 connecting to a logic PCB 95 which contains the analog-to-digital converter and a memory buffer to store the energy deposited in a detector pad element and the address of this pad. There are further provided two common logic PCB cards 96, 97 containing a main memory FIFO buffer, a logic controller and a BUS data transmitter which transmits serially the data in the FIFO to a receiver positioned in the data acquisition and display personal computer.

The collimator 90 may be of any suitable design and may have parallel holes, single or multiple pinholes and may be diverging or converging. The cross-section of the holes is either square, hexagonal or circular. To obtain the best intrinsic resolution a square hole cross-section is used for each hole facing a pad detector element. In other cases, the holes may not coincide geometrically with the detection pads.

In accordance with the present invention the camera head covers the entire field of view and in some embodiments motors may not be needed. However, in other embodiments one or two motors are used in either X or Y directions or in both X and Y directions, respectively. Using a motion in X or Y directions it makes it possible to oversample each pixel in X and/or the Y direction in any desired step. Using the Time Delay Integration (TDI) method it is possible to improve both the signal-to-noise ratio and the spatial resolution of the image.

The γ-camera heads according to the invention are suitable for use in the so-called Positron Emission Tomography (PET). One configuration for the performance of this technology is illustrated in FIG. 23. As shown, two light planar camera heads 100 according to the invention are positioned parallel to each other on opposite sides of the inspected organ 101 and operate in coincidence with each other. A β+ emitter such as F-18 is injected intravenously. When the β annihilates two 511 keV photons are emitted in exactly opposite directions, i.e., 180°. A true event is recorded only if two detection pad elements give simultaneously a signal for 511 keV. The position of the annihilation source is determined by the intersection of lines in which coincidence signal appears in the two lightweight camera heads. The camera head in this embodiment operates without collimators.

In another configuration of the PET technology the two camera heads may be in form of hemicylinder shells which enclose between them the inspected objects. Again, the two camera heads operate in coincidence with each other. The advantage of a cylinder shape is that it covers a larger solid angle than a planar camera head.

The suitability of a γ-camera head according to the invention for the PET technique is due to (i) its light weight and (ii) the large number of detector pads in one head (of the order of 10,000). Due to this large number of detector pads as distinct from the single large-size detector of the ANGER type γ-camera, each detector pad is exposed to a relatively low rate of gamma-interactions whereby the imaging electronics are simplified.

We claim:

1. A gamma-camera head having a detector assembly for the detection of X-rays and gamma-radiation, in which said detector assembly comprises an array of room temperature, solid state spectroscopy grade detectors capable of converting impinging X-rays and gamma radiation directly into electric signals which can be processed into an image, each of said spectroscopy grade detectors being associated with at least one collimator and with charge sensitive preamplifier means being a member selected from the group of preamplifiers, hybrid preamplifier/amplifier devices and application specific integrated circuits, which detectors and associated at least one collimator and preamplifier means are arranged in parallel rows extending in a first direction and suitably spaced from each other in a second direction normal to said first direction, each of said parallel rows holding a plurality of said room temperature spectroscopy grade solid state detectors;

whereby data acquired by said detector assembly is directly converted into an image.

2. A gamma-camera head according to claim 1, comprising parallel detector assemblies each including at least two juxtaposed detector rows.

3. A gamma-camera head according to claim 1, wherein the detectors and associated collimators and preamplification means are arranged in assemblies each comprising at least two juxtaposed and staggered detector rows and a plurality of such assemblies are arranged in parallel rows extending in the first direction and suitably spaced from each other in the second direction.

4. A gamma-camera head according to claim 1, wherein said room temperature, solid state spectroscopy grade detectors are arranged in groups of monolithic detectors having each a plurality of pad detector elements to form a two-dimensional array covering the complete field of view of the camera head.

5. A gamma-camera head according to claim 1, comprising electric motor means capable of moving said detector assembly in a stepwise fashion.

6. A gamma-camera head according to claim 5, wherein said electric motor means are capable of moving said detector assembly in a continuous fashion.

7. A gamma-camera head according to claim 6, wherein said motor means are capable of moving said detector assembly also in said first direction in a controlled fashion.

8. A gamma-camera head according to claim 7, comprising two separate electric motor means for moving the detector assembly in said first and second directions.

9. A gamma-camera head according to claim 7, comprising one single electric motor means for moving the detector assembly in said first and second directions.

10. A gamma-camera head according to claim 5, wherein said motor means are capable of moving said detector assembly also in said first direction in a controlled fashion.

11. A gamma-camera head according to claim 10, comprising two separate electric motor means for moving the detector assembly in said first and second directions.

12. A gamma-camera head according to claim 10, comprising one single electric motor means for moving the detector assembly in said first and second directions.

13. A gamma-camera head according to claim 1, wherein each of said room temperature, solid state spectroscopy grade detectors is a high atomic number room temperature spectroscopy grade detectors.

14. A gamma-camera head according to claim 13, wherein each of said room temperature, solid state spectroscopy grade detector is a member selected from the group consisting of CdTe, CdZnTe, $PbI_2$ and $HgI_2$.

15. A gamma-camera head according to claim 1, having a monolithic detector array and built-in densely packed analog amplifiers and multiplexing logic electronics.

16. A gamma-camera assembly comprising a γ-camera head according to claim 1 in association with at least one work station with a hardware/software combination that includes electronics, a man-machine interface module, a data acquisition module, an image reconstruction module and an image processing and display module.

17. A gamma-camera assembly according to claim 16, wherein the head is mounted on a long foldable arm, whereby a subject can be diagnosed from any desired direction.

18. A gamma-camera assembly according to claim 16, wherein the camera head is remote from at least one work station, comprising a remote station interface module.

19. A gamma-camera assembly according to claim 16, wherein the work station electronics include amplifier means for association with said preamplifier in the camera head.

20. A gamma-camera assembly according to claim 16, comprising means for time delay integration.

21. A gamma-camera assembly according to claim 16, being portable and comprising a lap-top computer, said camera head being portable.

22. A portable gamma-camera assembly according to claim 21, further comprising straps for attaching the camera head onto a diagnosed subject.

23. A portable gamma-camera assembly according to claim 21, comprising a foldable stand for holding the camera head in operation in close proximity to a diagnosed subject.

24. A light-weight gamma-camera head according to claim 1 for use in a planar γ-camera.

25. A light-weight gamma-camera head according to claim 1 for use in a single photon emission computerized tomography system (SPECT).

26. A gamma-camera head according, to claim 1, wherein a collimator associated with each detector is exchangeable.

27. A gamma-camera according to claim 1 wherein each of said at least one collimator holds a plurality of parallel channels.

28. A gamma-camera head according to claim 1, wherein each of said parallel rows of detectors comprises a plurality of monolithic detector arrays each holding a plurality of pad detection elements.

29. A gamma-camera head according to claim 28, wherein several detector arrays form together a detector unit.

30. A gamma-camera head according to claim 28, wherein each of said room temperature, solid state spectroscopy grade detectors holds four monolithic detector arrays.

31. A gamma-camera head having a detector assembly for the detection of x-rays and gamma-radiation, in which said detector assembly comprises an array of room temperature, solid state spectroscopy grade detectors capable of converting impinging X-rays and gamma radiation directly into electric signals which can be processed into an image, each of said spectroscopy grade detectors being associated with at least one collimator and with charge sensitive preamplifier means being a member selected from the group of preamplifiers, hybrid preamplifier/amplifier devices and application specific integrated circuits, which detectors and associated at least one collimator and preamplifier means are arranged in parallel rows extending in a first direction and suitably spaced from each other in a second direction normal to said first direction and forming a two-dimensional array covering the complete field of view of the camera head;

whereby data acquired by said detector assembly is directly converted into an image.

32. A gamma-camera head having a detector assembly for the detection of X-rays and gamma-radiation, comprising a plurality of room temperature solid state spectroscopic grade detectors capable of converting impinging X-rays and gamma radiation directly into electric signals which can be processed into an image, each of said spectroscopy grade detectors being associated with collimator means.

33. A gamma-camera head according to claim 32, wherein said plurality of room temperature solid state spectroscopic grade detectors are densely packed and form a two-dimensional array covering the complete field of view of the camera head.

* * * * *

UNITED STATES PATENT AND TRADEMARK OFFICE
CERTIFICATE OF CORRECTION

PATENT NO. : 5,939,724
DATED : August 17, 1999
INVENTOR(S) : Yosef EISEN, et al.

It is certified that error appears in the above-identified patent and that said Letters Patent is hereby corrected as shown below:

On the title page: Item [54] and Column 1, line 3,

--LIGHT WEIGHT GAMMA-CAMERA HEAD AND GAMMA-CAMERA ASSEMBLIES CONTAINING IT--.

Signed and Sealed this

Fourth Day of January, 2000

Attest:

Attesting Officer

*Acting Commissioner of Patents and Trademarks*